US010881862B2

(12) United States Patent
Ghosh

(10) Patent No.: US 10,881,862 B2
(45) Date of Patent: Jan. 5, 2021

(54) ESTIMATING RV-TIMINGS FROM LEFT VENTRICULAR (LV) SENSING TIMES FOR ADAPTIVE CARDIAC RESYNCHRONIZATION THERAPY USING DDD/VDD LV PACING WITHOUT A RIGHT VENTRICULAR (RV) LEAD

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 276 days.

(21) Appl. No.: 15/975,258

(22) Filed: May 9, 2018

(65) Prior Publication Data
US 2018/0326215 A1    Nov. 15, 2018

Related U.S. Application Data

(60) Provisional application No. 62/504,127, filed on May 10, 2017.

(51) Int. Cl.
*A61N 1/368*    (2006.01)
*A61N 1/365*    (2006.01)
(Continued)

(52) U.S. Cl.
CPC ......... *A61N 1/3682* (2013.01); *A61N 1/3688* (2013.01); *A61N 1/36592* (2013.01);
(Continued)

(58) Field of Classification Search
CPC .......... A61N 1/368; A61N 1/365; A61N 1/37; A61N 1/36514; A61N 1/3682;
(Continued)

(56) References Cited

U.S. PATENT DOCUMENTS 5,117,824 A    6/1992   Keimel
6,393,316 B1   5/2002   Gillberg et al.
(Continued)

FOREIGN PATENT DOCUMENTS

EP       2508227 A1       10/2012
WO    2014/178035 A1      11/2014

OTHER PUBLICATIONS (PCT/US2018/032056) PCT Notification of Transmittal of the International Search Report and the Written Opinion of the International Searching Authority, dated Jul. 6, 2018, 14 pages.
(Continued)

*Primary Examiner* — Jon Eric C Morales

(57) ABSTRACT

Methods and/or devices may be configured to estimate right ventricular-timings from left ventricular (LV) sensing times for adaptive cardiac therapy using DDD/VDD LV pacing without using a right ventricular (RV) lead. One embodiment employs a subcutaneous device (SD) in a patient and a leadless pacing device (LPD) coupled to a patient's heart. Heart activity including atrial and ventricular events are sensed from the patient's heart using the SD. Left ventricular events (LVS) are sensed using the LPD. The SD is used to determine whether cardiac resynchronization pacing therapy (CRT pacing) is appropriate based upon the heart activity sensed by the SD. The SD is further configured to determine timing of CRT pacing pulses for delivery to cardiac tissue through the LPD.

25 Claims, 13 Drawing Sheets

(51) Int. Cl.
  *A61N 1/39* (2006.01)
  *A61N 1/375* (2006.01)
  *A61N 1/05* (2006.01)
  *A61N 1/37* (2006.01)
  *A61N 1/362* (2006.01)

(52) U.S. Cl.
  CPC ......... *A61N 1/3756* (2013.01); *A61N 1/3962* (2013.01); *A61N 1/39622* (2017.08); *A61N 1/0504* (2013.01); *A61N 1/057* (2013.01); *A61N 1/0563* (2013.01); *A61N 1/3621* (2013.01); *A61N 1/36585* (2013.01); *A61N 1/36843* (2017.08); *A61N 1/371* (2013.01)

(58) Field of Classification Search
  CPC ............... A61N 1/36842; A61N 1/3684; A61N 1/37264; A61N 1/37247; A61B 5/00; A61B 5/0408; A61B 5/04085; A61B 5/6823
  USPC ........................................................ 607/17
  See application file for complete search history.

(56) References Cited

U.S. PATENT DOCUMENTS

| | | |
|---|---|---|
| 6,512,940 B1 | 1/2003 | Brabec |
| 6,522,915 B1 | 2/2003 | Ceballos |
| 6,622,046 B2 | 9/2003 | Fraley |
| 7,941,218 B2 | 5/2011 | Sambelashvili et al. |
| 8,145,308 B2 | 3/2012 | Sambelashvili et al. |
| 8,214,041 B2 | 7/2012 | Van Gelder et al. |
| 8,744,572 B1 | 6/2014 | Greenhut |
| 8,923,963 B2 | 12/2014 | Bonner |
| 9,132,274 B2 | 9/2015 | Ghosh |
| 9,403,019 B2 | 8/2016 | Sambelashvili |
| 9,717,923 B2 | 8/2017 | Thompson-Nauman |
| 9,789,319 B2 | 10/2017 | Sambelashvili |
| 9,808,633 B2 | 11/2017 | Bonner |
| 2003/0083709 A1 | 5/2003 | Zhu et al. |
| 2011/0029034 A1 | 2/2011 | Fischer et al. |
| 2015/0142069 A1 | 5/2015 | Sambelashvili |
| 2016/0045738 A1* | 2/2016 | Ghosh ................ A61B 5/04085 607/17 |
| 2016/0158567 A1 | 6/2016 | Marshall |

OTHER PUBLICATIONS

Medtronic Amplia MRI™ Quad CRT-D Surescanᴠ DTMB2Q1 Device Manual, Jan. 5, 2016, 62 pages.

* cited by examiner

ESTIMATING RV-TIMINGS FROM LEFT VENTRICULAR (LV) SENSING TIMES FOR ADAPTIVE CARDIAC RESYNCHRONIZATION THERAPY USING DDD/VDD LV PACING WITHOUT A RIGHT VENTRICULAR (RV) LEAD

CROSS-REFERENCE TO RELATED APPLICATIONS

This application claims the benefit of U.S. Provisional Patent Application 62/504,127 entitled "ESTIMATING RV-TIMINGS FROM LEFT VENTRICULAR (LV) SENSING TIMES FOR ADAPTIVE CARDIAC RESYNCHRONIZATION THERAPY USING DDD/VDD LV PACING WITHOUT A RIGHT VENTRICULAR (RV) LEAD" and filed on May 10, 2017, which is incorporated herein by reference in its entirety.

BACKGROUND

In the normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers causing a depolarization and the resulting atrial chamber contractions. The excitation pulse is further transmitted to and through the ventricles via the atrioventricular (AV) node and a ventricular conduction system causing a depolarization and the resulting ventricular chamber contractions.

Disruption of this natural pacing and conduction system as a result of aging or disease can be treated by artificial cardiac pacing. For example, one or more heart chambers may be electrically paced depending on the location and severity of the conduction disorder. In addition, cardiac pacing for ventricular dyssynchrony, often referred to as cardiac resynchronization therapy (CRT), may include pacing one or both ventricles before normal conduction through the AV node depolarizes the ventricles.

Implantable medical devices (IMDs) are capable of utilizing pacing therapies, such as CRT, to maintain hemodynamic benefits to patients. Pacing therapy may be delivered from an implantable generator, through a lead, and into the patient's heart. A conventional IMD, configured to deliver CRT pacing, typically comprises the IMD, a left ventricular lead, a right ventricular lead, and an atrial lead. The left ventricular lead and the right ventricular leads are typically used to deliver pacing pulses to one or both the ventricles so that both ventricles contract in synchrony with each other. The atrial lead is typically used to sense the atrial activity so that delivery of the pacing pulses occurs A conventional IMD then uses data that is sensed from heart activity to determine basic programmable pacing parameters. Basic programmable pacing parameters include atrioventricular delay (AV delay), left ventricle to right ventricle delay (VV delay), pacing amplitude, pacing rate, pulse duration, and pacing pathway or vector (e.g., bipolar such as a lead tip electrode to a lead ring electrode, etc. or unipolar such as a lead tip electrode to IMD casing, or housing), which all may be configured to ensure effective therapy to the patient.

It is desirable to develop new pacing systems that are able to efficiently and cost-effectively pace cardiac tissue.

SUMMARY

A subcutaneous device (SD) is in electrical communication with a leadless pacing device (LPD) for delivery of cardiac therapy. The SD includes a therapy delivery module, a sensing module, and a control module coupled to the therapy delivery module and to the sensing module. The therapy delivery module is configured to signal the LPD to deliver pacing therapy to either the left ventricle and/or the right ventricle of a patient's heart using at least one electrode on the LPD. The sensing module may be configured to sense electrical activity of the patient's heart (e.g., electrical activity of the left or right atrium) using at least one subcutaneous electrode located on the housing of the SD and/or a medical electrical lead extending from the SD. The control module may be configured to control the delivery of pacing therapy via the LPD to either the left ventricle or the right ventricle of a patient's heart based on an AV delay (where the pacing therapy is delivered over a plurality of heartbeats) and sense electrical activity of the patient's heart using the sensing module during the delivery of the pacing therapy. The control module may be further configured to measure a ventricular activation time for each of the plurality of heartbeats. The control module can be further configured to measure a ventricular activation time for each of the plurality of heartbeats between the delivery of pacing stimulus of the pacing therapy and at least one selected fiducial point of the sensed electrical activity (e.g., a maximum negative slope of the far-field electrical activity of the right ventricle of the patient's heart, a maximum value of the near-field electrical activity of the right ventricle of the patient's heart, etc.) resulting from at least one of the delivered pacing stimulus of the pacing therapy and an intrinsic conduction of the patient's heart. The processor of the IMD is configured to determine the onset of baseline QRS (Qon) timing from the sensed heart activity. The processor calculates atrial event-Qon timing. Atrial event includes intrinsic (e.g., natural activity denoted as As) or paced atrial activity denoted as Ap. The processor further measures baseline atrial event-ventricular event to obtain $\Delta t$ timing. The processor subtracts atrial event-Qon from A-LVs to estimate the A-RV delay. The processor then updates the AV delay using the estimated A-RV for delivery of cardiac resynchronization therapy. Thereafter, subsequent electrical signals are sensed from the patient's heart using the SD. Based on the subsequent electrical signals, the SD determines whether the CRT pacing by the LPD provided efficacious resynchronization and whether the delivery and timing of subsequent CRT pacing pulses should be modified.

Yet another embodiment relates to using a subcutaneous device (SD) in a patient and a leadless pacing device (LPD) coupled to a patient's heart. Heart activity including atrial and ventricular events is sensed from the patient's heart using the SD. Left ventricular events (LVS) are sensed using the LPD. A determination is made as to whether cardiac resynchronization pacing therapy (CRT pacing) is appropriate based upon the heart activity sensed using the SD.

A determination is made involving timing of CRT pacing pulses for delivery to cardiac tissue through the LPD, wherein determining the timing of the CRT pacing pulses comprises a series of steps. For example, an atrial event is detected and onset of baseline QRS (Qon) is determined from the heart activity sensed using the SD. An atrial event to Qon interval is measured. An atrial event to LVs interval is measured. The atrial event to Qon interval is subtracted from a time interval "t" from the atrial event to LVs interval to obtain a correction factor. The correction factor is used to obtain a new pacing delay. Thereafter CRT pacing pulses are delivered to the heart using the LPD and using the new pacing delay.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
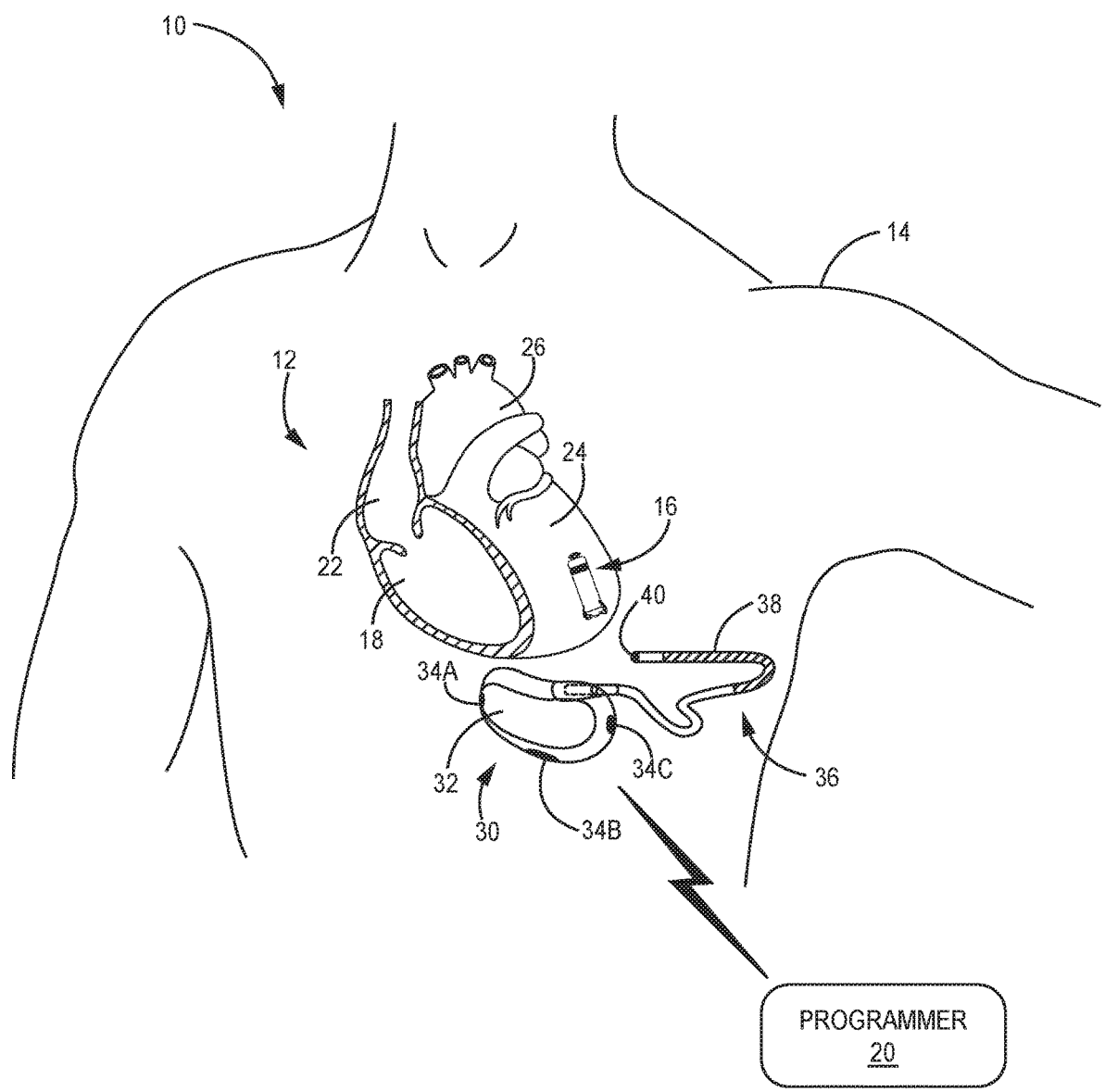
FIG. 1 is a conceptual drawing illustrating an example system that includes a subcutaneous implantable cardioverter defibrillator (SD) implanted exterior to the rib cage of a patient and a leadless pacing device (LPD) implanted within a cardiac chamber of the patient.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, devices, and systems shall be described with reference to FIGS. 1-10. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Figure 7A:
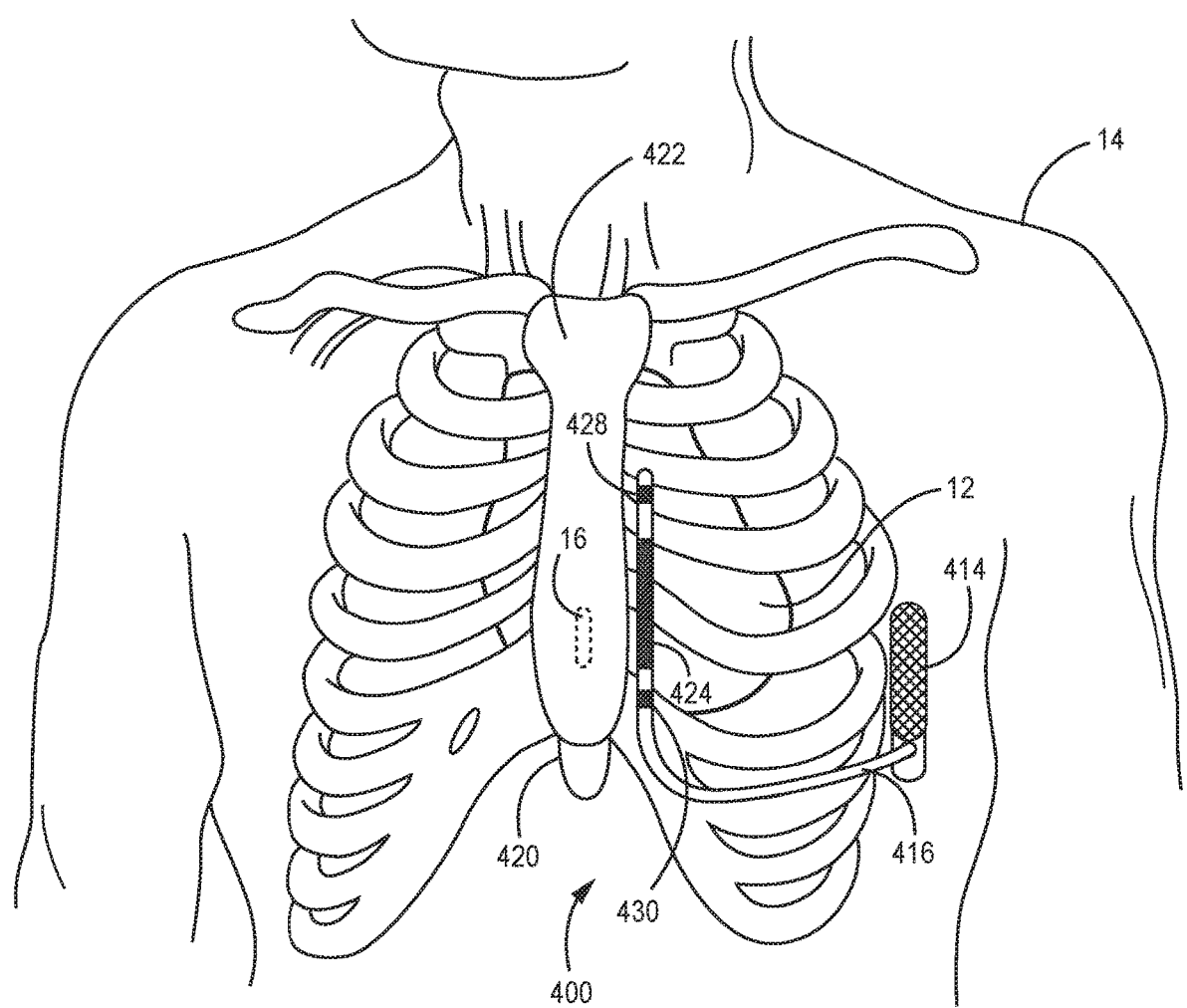
FIG. 7A is a front view of a patient implanted with the extracardiovascular ICD system implanted intra-thoracically.

The present disclosure relates to pacing systems and/or methods that are configured to deliver CRT pacing without employing a right ventricular lead to pace and/or sense heart activity from the RV. Pacing systems that lack a RV lead are configured to estimate right ventricular (RV)-timings in order to adjust pacing parameters (e.g. W delay, AV delay etc.). Estimating RV timing involves several steps. The atrial event (e.g. Atrial sense) to Qon interval (As-Qon) is determined. An atrial sensed (As) signal can be acquired from an electrode on or near the atrium without an atrial lead. For example, As can be acquired from the electrode, located on a substernal lead, and positioned as shown in FIG. 7A. Another example is obtaining a far-field ECG signal in a leadless embodiment shown in FIG. 7A without an RV lead. Far field is defined as the electrode that is the greatest distance away from the pacing electrode.

Qon can be periodically measured by the IMD every week using far-field signal (i.e. LV tip-Can for the leaded embodiment or substernal ECG signal acquired by the leadless embodiment shown in FIG. 7A). After determining As-Qon, a time constant t is added to As-Qon. Time constant t is a constant parameter representing a difference between onset of QRS and RV sense timing from data collected from a group of patients having an implanted RV lead. Thereafter, one or more pacing parameters can be optimized. To illustrate, sensed atrioventricular delay/paced atrioventricular delay (SAV/PAV) for CRT is calculated. For example, optimal SAV/PAV for therapy is determined based on 0.7*(As-LVs−d.) where d is the difference between LV sensing time measured by electrodes directly in contact with LV (e.g. LPD or a LV lead) and the estimated RV sensing time that may be computed apriori by the device.

A variety of pacing modes can implement the present disclosure. Exemplary pacing modes that can be used to deliver CRT without a RV lead include a dual chamber pacemaker using DDD (i.e. dual pacing of the atria and left ventricle, dual atrial and left ventricular sensing, and dual response (inhibited and/or triggered) to sensing, and DDD/VDD LV pacing.

VDD pacing mode, uses a single ventricular lead with sensing rings in the right atrium, to sense atrial activity and then monitor AV conduction or alternatively it may involve subcutaneous or substernal device with sensing leads in the subcutaneous or substernal space for sensing P-waves (atrial activity) in communication (e.g. through TCC or RF) with a LPD in the left ventricle.

For some patients suffering from heart failure and intraventricular conduction delays due to, e.g., left bundle branch block (LBBB), right bundle branch block (RBBB), the delivery of CRT can occur due to a single ventricular pacing stimulus by pre-exciting the ventricle with conduction delay. Such a stimulus must be properly timed relative to intrinsic depolarization of the other, non-delayed ventricle. This phenomenon may be referred to herein as "fusion pacing" since ventricular activation from a pacing stimulus fuses or merges with ventricular activation from intrinsic conduction. When the ventricular pacing stimulus is properly timed a desired ventricular resynchronization results with a minimum of pacing energy, thereby extending the operating life of an implantable pulse generator (e.g., an implantable cardioverter-defibrillator, pacemaker, and the like). Moreover, in some cases a more effective or physiologic form of CRT delivery can be achieved since the system and methods herein utilize a portion of intrinsic activation, which can be superior to an entirely evoked (e.g., paced) form of CRT. Fusion pacing may also be referred to herein as left ventricle-only pacing or right ventricle-only pacing.

One method of fusion pacing, or left ventricle-only pacing, includes pacing the left ventricle at an appropriate time to achieve fusion of a paced wavefront with an intrinsic depolarization of the right ventricle. One method of fusion pacing, or left ventricle-only pacing, includes pacing the left ventricle at an appropriate time to achieve fusion of a paced wavefront with an intrinsic depolarization of the right ventricle. Such a CRT method may reduce device power output relative to biventricular pacing and may improve hemodynamics, especially at lower heart rates.

One specific parameter that may be used by an IMD to deliver cardiac therapy (e.g., CRT such as left ventricular fusion pacing (also referred to as monoventricular pacing) is an atrioventricular delay (AV delay), which may generally be described as a programmable value representing a time period between atrial electrical activity, whether intrinsic (e.g., natural) or paced, and the delivery of ventricular pacing. The optimal value of the AV delay has generally been defined as a delay that produces the maximum stroke volume for a fixed heart rate or the maximum cardiac output for a sinus node driven heart rate.

To optimize or adjust the AV delay, a cardiac therapy device such as an IMD may measure a patient's intrinsic AV conduction time. A patient's intrinsic AV conduction time is the time between an intrinsic atrial event (e.g., depolarization of the right atrium) and an intrinsic ventricular event (e.g., depolarization of the right ventricle). As used herein, an "intrinsic" event or conduction is one that occurs or is conducted naturally (e.g., an intrinsic ventricular event is an event triggered by electrical activity transmitted across the AV node of the heart from the atria to the ventricles, etc.). A cardiac therapy device may periodically measure a patient's intrinsic AV conduction time, or interval, and adjust the AV delay in response to the measured intrinsic AV conduction time, e.g., to optimize cardiac functionality.

For example, a CRT algorithm (e.g., performed by an IMD) may measure a patient's intrinsic AV conduction time once every minute by forcing delays used for ventricular pacing (e.g., paced AV delay, sensed AV delay, etc.) to long values (e.g., 300 milliseconds (ms), 350 ms, etc.). Conventionally, the intrinsic AV conduction time measurement has been performed periodically (e.g., every 60 seconds) so that the CRT algorithm can adapt to changes in the patient's intrinsic AV conduction time. An example of adaptive CRT therapy is shown and described in U.S. Pat. No. 9,403,019 filed Jan. 30, 2012, and U.S. Pat. No. 9,789,319, incorporated herein by reference in their entirety.

In other words, CRT algorithms may temporarily suspend, or interrupt, pacing therapy for one or more heartbeats to measure a patient's intrinsic AV conduction time for use in modifying or adjusting (e.g., optimizing) one or more pacing parameters such as AV delay.

One or more exemplary methods and devices described herein may provide frequent adjustment of left ventricular (LV) pace timing without periodic withholding of pacing therapy (e.g., CRT) to measure a patient's intrinsic AV conduction time. In at least one embodiment, a far-field or near-field right ventricular electrogram (EGM) may be monitored close to the timing of a LV pace. For the far-field EGM, the peak negative slope of the EGM may indicate local right ventricular (RV) activation. For the near-field EGM, the absolute peak EGM amplitude may indicate local RV activation. The timing of the local RV activation relative to the delivery of the LV pace, which is the measured right ventricular activation time, may be used to adjust future LV pacing timing (e.g., the AV delay).

The sensing module 86 is coupled (e.g., electrically coupled) to sensing apparatus, which may include, among additional sensing apparatus, the electrodes 40, 42, 44, 46, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

If IMD 16 is configured to generate and deliver pacing pulses to the heart 12, the control module 81 may include a pacer timing and control module, which may be embodied as hardware, firmware, software, or any combination thereof. The pacer timing and control module may include one or more dedicated hardware circuits, such as an ASIC, separate from the processor 80, such as a microprocessor, and/or a software module executed by a component of processor 80, which may be a microprocessor or ASIC. The pacer timing and control module may include programmable counters which control the basic time intervals associated with DDD, WI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Generally, one or more parameters of CRT (e.g., pacing parameters) may be adjusted, or modified, based on one or more sensed physiological signals, etc., to, e.g., deliver effective cardiac therapy to a patient. One parameter of CRT that may be adjusted is an AV delay, which may be used to determine when to deliver ventricular pacing based on either sensed intrinsic atrial activity or paced atrial activity. Often, the AV delay may be adjusted based on a measurement of a patient's intrinsic AV conduction time. To measure a patient's intrinsic AV conduction time, CRT methods and devices may temporarily suspend pacing therapy for one or more heartbeats such that the natural depolarization of the patient's heart may be monitored.

Figure 10:
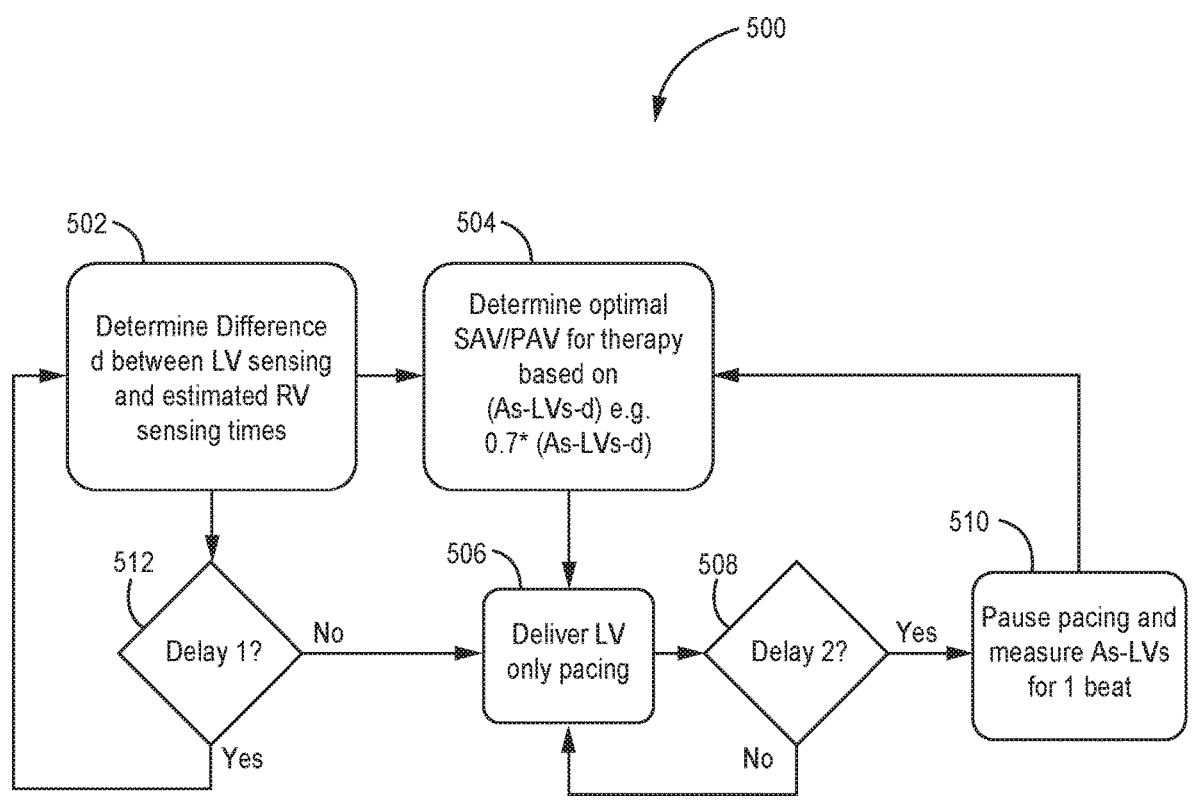
FIG. 10 is a flow chart of an exemplary method of adaptive left ventricular pacing without employing a right ventricular medical electrical lead.

The present disclosure is shown and described relative to exemplary method 300 (FIG. 8) and method 500 (FIG. 10). FIGS. 1-7 depict and describe various cardiac pacing systems including implantable devices configured to execute methods 300 or 500. Methods 300 or 500 adjust a pacing parameter (e.g. AV delay etc.) without temporarily suspending pacing therapy by using ventricular activation times monitored during pacing therapy. For example, ventricular activation times may be associated, or correlated, with optimal timings for the delivery of ventricular pacing (e.g., LV-only pacing, RV-only pacing, biventricular pacing, etc.), and thus, ventricular activation times monitored during pacing therapy may be used to adjust one or more pacing parameters such as, e.g., AV delay (which is used to determine when to deliver ventricular pacing).

FIG. 1 is a conceptual drawing illustrating an example system 10 that includes a subcutaneous device (SD) 30 (e.g. subcutaneous-implantable cardioverter-defibrillator (S-ICD), loop recorder (i.e. REVEAL®) etc.) implanted exterior to a rib cage of patient 14 and a leadless pacing device (LPD) 16 implanted within right ventricle 18 of patient 14. The SD 30 can be implanted external to a rib cage and within the vasculature. Additionally or alternatively, an implantable medical device can be implanted substernally/retrosternally, as described in U.S. Pat. No. 9,717,923, entitled "IMPLANTABLE MEDICAL DEVICE SYSTEM HAVING IMPLANTABLE CARDIAC DEFIBRILLATOR SYSTEM AND SUBSTERNAL LEADLESS PACING DEVICE" filed May 6, 2013, incorporated by reference in its entirety. In the example of FIG. 1, system 10 includes LPD 16 and SD 30. External programmer 20 may be configured to communicate with one or both of LPD 16 and SD 30. SD 30 and LPD 16 can be configured to communicate in a master-slave communication mode. Generally, there are no wires or other direct electrical (e.g., hardwired) connections between SD 30 and LPD 16. In this manner, any communication between SD 30 and LPD 16 may be described as "wireless" communication. Patient 14 is ordinarily, but not necessarily, a human patient.

Exemplary SD 30 includes a housing 32 configured to be subcutaneously implanted outside the rib cage of patient 14. The subcutaneous implantation location may be anterior to the cardiac notch, for example. In addition, housing 32 may carry three subcutaneous electrodes 34A-34C (collectively "electrodes 34"). In other examples, housing 32 may carry fewer or greater than three electrodes. Lead 36 may be configured to couple to housing 32 and extend from housing 32 to a different subcutaneous location within patient 14. For example, lead 36 may be tunneled laterally and posteriorly to the back of patient 14 at a location adjacent to a portion of a latissimus dorsi muscle. Lead 36 may carry electrode coil 38 along a length of lead 36 and sensing electrode 40 at a distal end of lead 36. SD 30 may be configured such that heart 12 may be disposed at least partially between housing 30 and electrode coil 38 of lead 36. In some examples, lead 36 may carry two or more electrode coils 38 and/or two or more sensing electrodes 40.

SD 30 may contain, within housing 32, signal processing and therapy delivery circuitry to detect cardiac conditions (e.g., ventricular dyssnchrony, arrhythmias such as bradycardia and tachycardia conditions etc.) and to communicate with LPD 16 to apply appropriate electrical stimuli (e.g. pacing and/or anti-tachyarrhythmia shock therapy (e.g., defibrillation or cardioversion shocking pulses)) to heart 12. SD 30 also may be configured to apply pacing pulses via one or more electrodes 34. SD 30 may be configured to apply the anti-tachyarrhythmia shock pulses between coil electrode 38 and one or more of electrodes 34 and/or the electrically conductive housing 32 (e.g., an additional can electrode) of SD 30. SD 30 may be configured to communicate with programmer 20 via an RF communication link, inductive coupling, or some other wireless communication protocol.

SD 30 differs from traditionally used ICDs in that housing 32 may be larger in size than the housing of a traditional ICD to accommodate larger capacity batteries, for example. In addition, SD 30 may be implanted subcutaneously whereas a traditional ICD may be implanted under muscle or deeper within patient 14. In other examples, housing 32 may be shaped or sized differently to be implanted subcutaneously instead of under a muscle or within deep tissue. Moreover, SD 30 does not include leads configured to be placed in the bloodstream (e.g., endocardial or epicardial leads). Instead, SD 30 may be configured to carry one or more electrodes (e.g., electrodes 34) on housing 32 together with one or more subcutaneous leads (e.g., lead 36) that carry defibrillation coil electrode 38 and sensing electrode 40. In other examples, lead 36 may include additional electrodes. These subcutaneously implanted electrodes of SD 30 may be used to provide therapies similar to that of traditional ICDs without invasive vascular leads. In other examples, the exact configuration, shape, and size of SD 30 may be varied for different applications or patients. Although SD 30 is generally described as including one or more electrodes, SD 30 may typically include at least two electrodes to deliver an electrical signal (e.g., therapy) and/or provide at least one sensing vector. Other exemplary SDs 30 can be used in combination with LPD 16. For example, SD 30 includes intravenously implanted device (IID), an ICD or a pacemaker or any other suitable device.

System 10 also includes one or more LPDs, such as LPD 16. LPD 16 may be, for example, an implantable leadless pacing device (e.g., a pacemaker, cardioverter, and/or defibrillator) that provides electrical signals to heart 12 via electrodes carried on the housing of LPD 16. In the example of FIG. 1, LPD 16 is implanted within left ventricle 16 of heart 12 to sense electrical activity of heart 12 and/or deliver electrical stimulation, e.g., CRT such as fusion pacing, to heart 12. Fusion pacing involves left ventricle (LV) 24 only pacing with a pacing electrode on the LPD 16 in coordination with the intrinsic right ventricle (RV) activation. The present disclosure is directed to left ventricular fusion pacing. However, fusion pacing can also involve pacing the RV with a pacing electrode on the LPD 16 in coordination with the intrinsic LV activation. In this scenario, the LPD 16 is placed within the right ventricle 18.

LPD 16 is schematically shown in FIG. 1 attached to a wall of the left ventricle 24 via one or more fixation elements (e.g. tines, helix etc.) that penetrate the tissue. These fixation elements may secure LPD 16 to the cardiac tissue and retain an electrode (e.g., a cathode or an anode) in contact with the cardiac tissue. LPD 16 may also include one or more motion sensors (e.g., accelerometers) configured to detect and/or confirm cardiac conditions (e.g. ventricular dyssynchrony, tachyarrhythmias etc.) from these mechanical motions of heart 12. Since LPD 16 includes two or more electrodes carried on the exterior housing of LPD 16, no other leads or structures need to reside in other chambers of heart 12. However, in other examples, system 10 may include additional LPDs within respective chambers of heart 12 (e.g., left atrium 26, right atrium 22).

Using the electrodes carried on the housing of LPD 16 may be capable sensing intrinsic electrical signals, e.g., an electrocardiogram (ECG). SD 30 may similarly sense intrinsic electrical signals from the sensing vectors of electrodes 34, 38, and 40. These intrinsic signals may be electrical signals generated by cardiac muscle and indicative of depolarizations and repolarizations of heart 12 at various times during the cardiac cycle. LPD 16 may generate an electrogram from these cardiac signals that may be used by LPD 16 to detect cardiac conditions (e.g. ventricular dyssynchrony, arrhythmias, such as tachyarrhythmias), or identify other cardiac events, e.g., ventricle depolarizations or atrium depolarizations. LPD 16 may also measure impedances of the carried electrodes and/or determine capture thresholds of those electrodes intended to be in contact with cardiac tissue. In addition, LPD 16 may be configured to communicate with external programmer 20. The configurations of electrodes used by LPD 16 for sensing and pacing may be typically considered bipolar but unipolar may also be used.

External programmer 20 may be configured to communicate with one or both of SD 30 and LPD 16. In examples where external programmer 20 only communicates with one of SD 30 and LPD 16, the non-communicative device may receive instructions from or transmit data to the device in communication with programmer 20. In some examples, programmer 20 comprises a handheld computing device, computer workstation, or networked computing device. Programmer 20 may include a user interface that receives input from a user. In other examples, the user may also interact with programmer 20 remotely via a networked computing device. The user may interact with programmer 20 to communicate with LPD 16 and/or SD 30. For example, the user may interact with programmer 20 to send an interrogation request and retrieve therapy delivery data, update therapy parameters that define therapy, manage communication between LPD 16 and/or SD 30, or perform any other activities with respect to LPD 16 and/or SD 30. Although the user is a physician, technician, surgeon, electrophysiologist, or other healthcare professional, the user may be patient 14 in some examples.

Programmer 20 may also allow the user to define how LPD 16 and/or SD 30 senses electrical signals (e.g., ECGs), detects cardiac conditions (e.g. ventricular dyssynchrony, arrhythmias etc.), delivers therapy, and communicates with other devices of system 10. For example, programmer 20 may be used to change detection parameters. In another example, programmer 20 may be used to manage therapy parameters that define therapies such as CRT. Moreover, programmer 20 may be used to alter communication protocols between LPD 16 and SD 30. For example, programmer 20 may instruct LPD 16 and/or SD 30 to switch between one-way and two-way communication and/or change which of LPD 16 and/or SD 30 are tasked with initial detection of a cardiac condition.

Programmer 20 may communicate with LPD 16 and/or SD 30 via wireless communication using any techniques known in the art. Examples of communication techniques may include, for example, radiofrequency (RF) telemetry, but other techniques are also contemplated. In some examples, programmer 20 may include a programming head that may be placed proximate to the patient's body near the LPD 16 and/or SD 30 implant site in order to improve the quality or security of communication between LPD 16 and/or SD 30 and programmer 20.

LPD 16 and SD 30 may engage in communication to facilitate the appropriate detection of ventricular dyssynchrony and/or delivery of CRT. The communication may include one-way communication in which one device is configured to transmit communication messages and the other device is configured to receive those messages. The communication may instead include two-way communication in which each device is configured to transmit and receive communication messages. LPD 16 and SD 30 may be configured to communicate with each other provide alternative electrical stimulation therapies.

Although LPD 16 may at least partially determine whether or not LPD 16 delivers CRT or another therapy to patient 14, LPD 16 may perform one or more functions in response to receiving a request from SD 30 and without any further analysis by LPD 16. In this manner, SD 30 may act as a master device and LPD 16 may act as a slave device. In this configuration, LPD 16 passively senses. Specifically, a VVT mode is employed as a trigger mode to pace in synchrony. In one or more embodiments, the LPD 16 can be configured to actively sense.

Figure 2A:
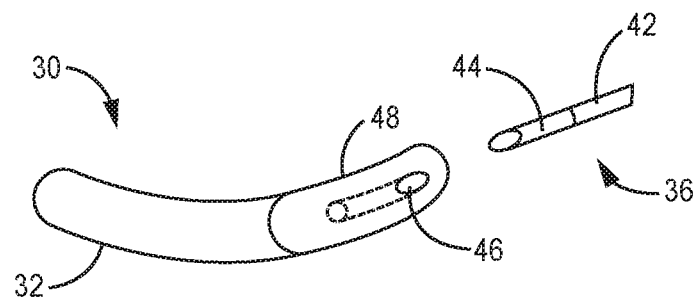
FIG. 2A is a conceptual drawing illustrating an example SD of FIG. 1.
Figure 2B:
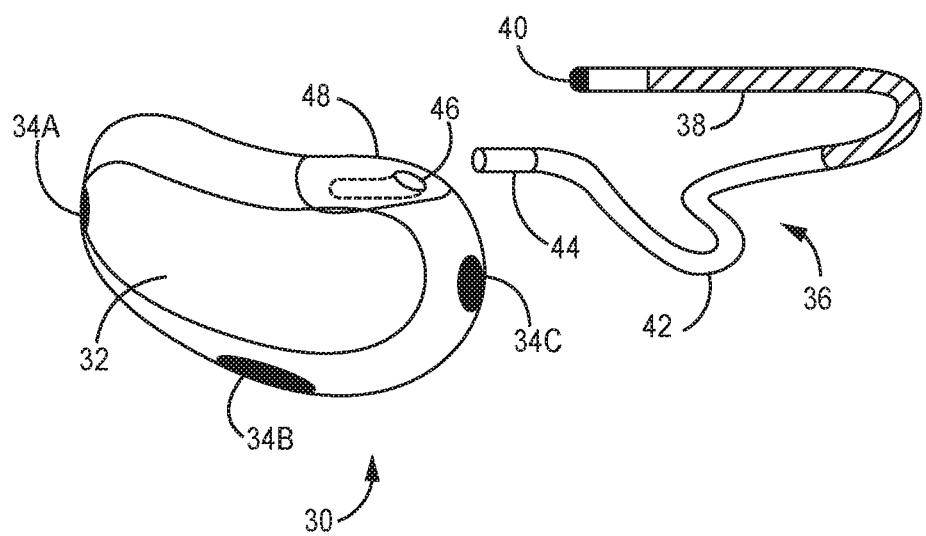
FIG. 2B is a conceptual drawing illustrating an example SD of FIG. 1.

FIGS. 2A and 2B are conceptual drawings illustrating different views of SD 30 of FIG. 1. FIG. 2A is a top view of SD 30, and FIG. 2B is a front view of SD 30. In the example of FIGS. 2A and 2B, housing 32 may be constructed as an ovoid with a substantially kidney-shaped profile or any other suitable shape such as that which is shown in FIG. 7D. The ovoid shape of housing 32 may promote ease of subcutaneous implantation and may minimize patient discomfort during normal body movement and flexing of the thoracic musculature. In other examples, housing 32 may be constructed with different shapes intended for different implant locations and/or to house different components, subcutaneous leads, or configurations for electrodes 34 FIG. 2B.

Housing 32 may contain the electronic circuitry of SD 30. Header 48 and connector 46 may provide an electrical connection between distal electrode coil 38 and distal sensing electrode 40 of lead 36 and the circuitry within housing 32. Subcutaneous lead 36 may include distal defibrillation coil electrode 38, distal sensing electrode 40, insulated flexible lead body 42 and proximal connector pin 44. Distal sensing electrode 40 may be sized appropriately to match the sensing impedance of electrodes 34A-34C to be used in combination.

In some examples, electrodes 34 are each welded into place on a flattened periphery of housing 32 and are connected to electronic circuitry inside housing 32. Electrodes 34 may be constructed of flat plates, or alternatively, spiral electrodes (as described in U.S. Pat. No. 6,512,940, incorporated herein in its entirety) and mounted in a non-conductive surround shroud (as described in U.S. Pat. Nos. 6,522,915 and 6,622,046, both incorporated herein in their entirety). Electrodes 34 shown in FIG. 2B may be positioned on housing 32 to form orthogonal signal vectors. However, electrodes 34 may be positioned to form any non-orthogonal signal vectors in other examples. In addition, housing 32 may include fewer or greater than three electrodes. Moreover, housing 32 may be configured as an electrically conductive surface and operate as an electrode. Housing 32 may be referred to as a "can electrode" or used as an indifferent electrode. In some examples, housing 32 may be used as an electrode with coil electrode 38 during delivery of (electrical stimuli e.g. pacing pulses, anti-tachyarrhythmia shock).

Figure 3:
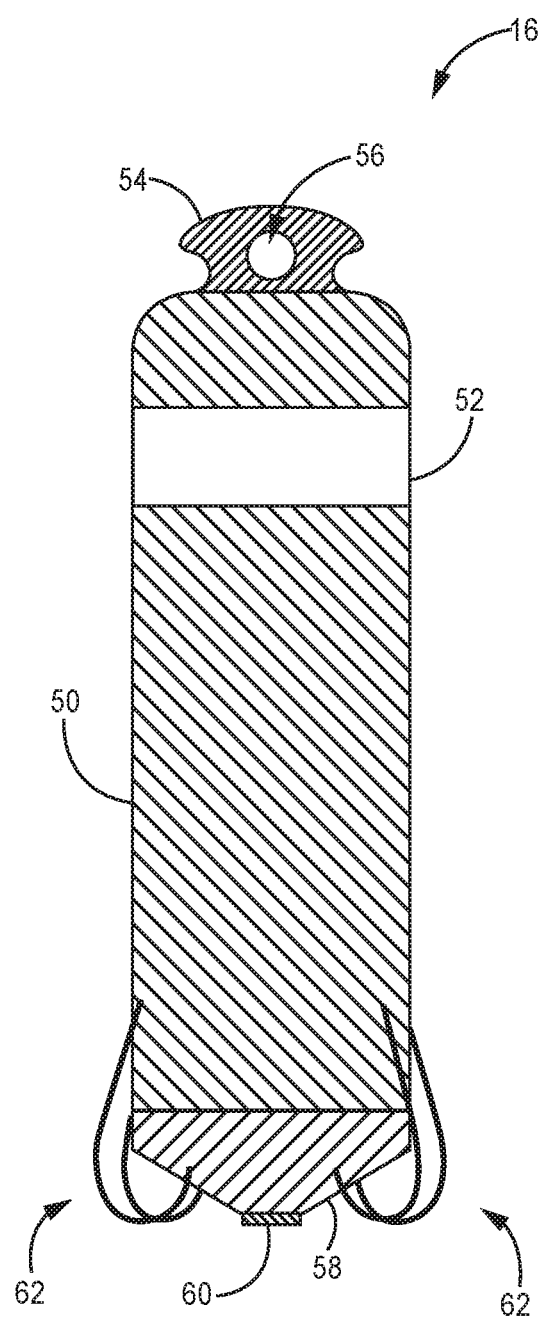
FIG. 3 is a conceptual drawing illustrating the example LPD of FIG. 1.

FIG. 3 is a conceptual drawing illustrating example LPD 16 of FIG. 1. An exemplary LPD 16 can be MICRA™ commercially available from Medtronic Plc, located in Dublin, Ireland. As shown in FIG. 3, LPD 16 includes case 50, cap 58, electrode 60, electrode 52, fixation mechanisms 62, flange 54, and opening 56. Together, case 50 and cap 58 may be considered the housing of LPD 16. In this manner, case 50 and cap 58 may enclose and protect the various electrical components within LPD 16. Case 50 may enclose substantially all of the electrical components, and cap 58 may seal case 50 and create the hermetically sealed housing of LPD 16. Although LPD 16 is generally described as including one or more electrodes, LPD 16 may typically include at least two electrodes (e.g., electrodes 52 and 60) to deliver an electrical signal (e.g., therapy such as CRT) and/or provide at least one sensing vector. Electrodes 52 and 60 are carried on the housing created by case 50 and cap 58. In this manner, electrodes 52 and 60 may be considered leadless electrodes. In the example of FIG. 3, electrode 60 is disposed on the exterior surface of cap 58. Electrode 60 may be a circular electrode positioned to contact cardiac tissue upon implantation. Electrode 52 may be a ring or cylindrical electrode disposed on the exterior surface of case 50. Both case 50 and cap 58 may be electrically insulating. Electrode 60 may be used as a cathode and electrode 52 may be used as an anode, or vice versa, for delivering CRT or other appropriate cardiac therapy (ATP, shock etc.). However, electrodes 52 and 60 may be used in any stimulation configuration. In addition, electrodes 52 and 60 may be used to detect intrinsic electrical signals from cardiac muscle. In other examples, LPD 16 may include three or more electrodes, where each electrode may deliver therapy and/or detect intrinsic signals. CRT delivered by LPD 16 may be considered to be "painless" to patient 14 or even undetectable by patient 14 since the electrical stimulation occurs very close to or at cardiac muscle and at relatively low energy levels compared with alternative devices.

Fixation mechanisms 62 may attach LPD 16 to cardiac tissue. Fixation mechanisms 62 may be active fixation tines, screws, clamps, adhesive members, or any other types of attaching a device to tissue. As shown in the example of FIG. 3, fixation mechanisms 62 may be constructed of a memory material that retains a preformed shape. During implantation, fixation mechanisms 62 may be flexed forward to pierce tissue and allowed to flex back towards case 50. In this manner, fixation mechanisms 62 may be embedded within the target tissue.

Flange 54 may be provided on one end of case 50 to enable tethering or extraction of LPD 16. For example, a suture or other device may be inserted around flange 54 and/or through opening 56 and attached to tissue. In this manner, flange 54 may provide a secondary attachment structure to tether or retain LPD 16 within heart 12 if fixation mechanisms 62 fail. Flange 54 and/or opening 56 may also be used to extract LPD 16 once the LPD needs to be explanted (or removed) from patient 14 if such action is deemed necessary.

In another example, LPD 16 may be configured to be implanted external to heart 12, e.g., near or attached to the epicardium of heart 12. An electrode carried by the housing of the fusion pacing LPD 16 may be placed in contact with the epicardium and/or one or more electrodes placed in contact with the epicardium at locations sufficient to provide therapy (e.g., on external surfaces of the left and/or right ventricles). In any example, SD 30 may communicate with one or more leadless or leaded devices implanted internal or external to heart 12.

Figure 4:
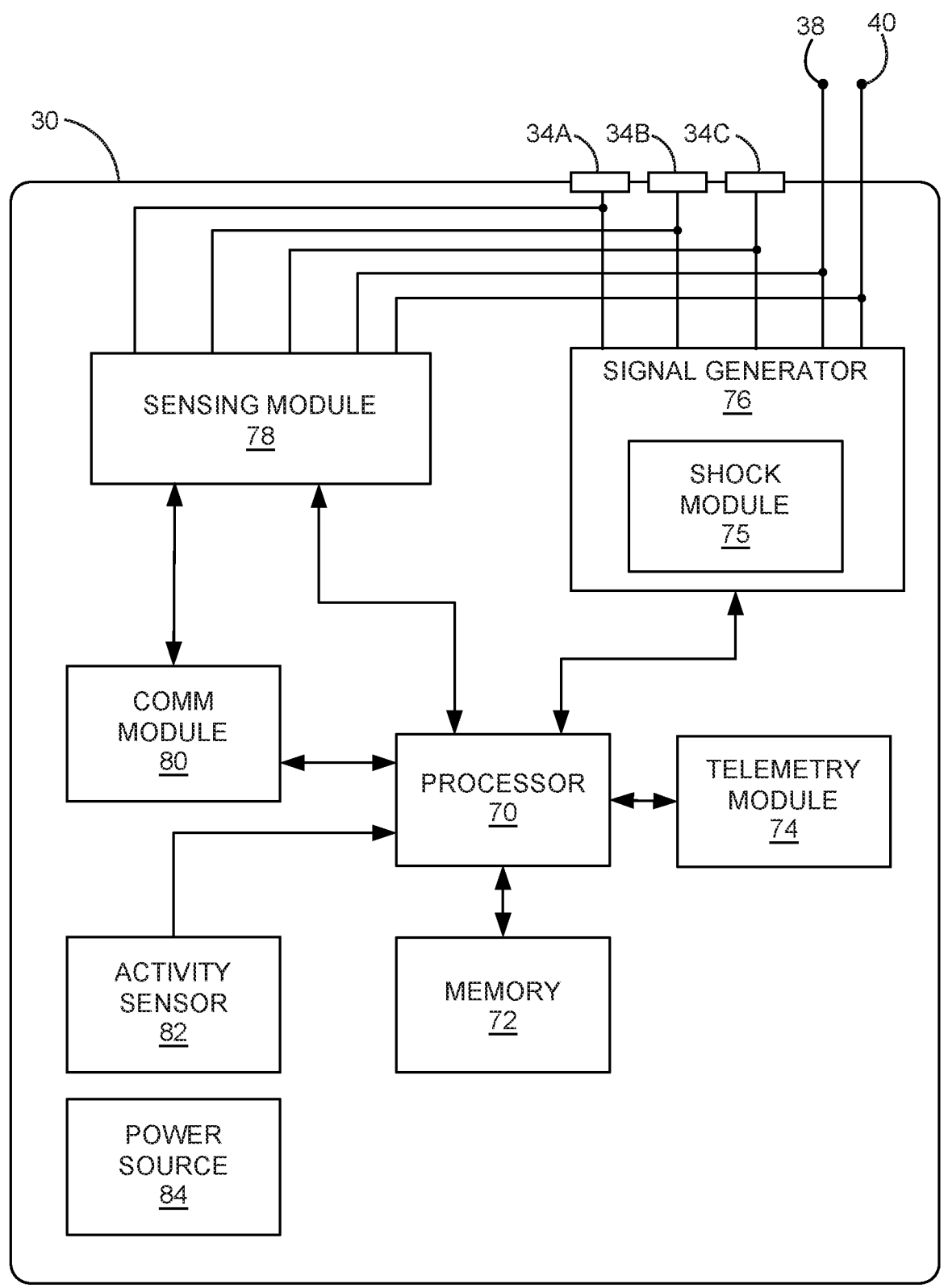
FIG. 4 is a functional block diagram illustrating an example configuration of the SD of FIG. 1.

FIG. 4 is a functional block diagram illustrating an example configuration of SD 30 of FIG. 1. In the illustrated example, SD 30 includes a processor 70, memory 72, shock module 75, signal generator 76, sensing module 78, telemetry module 74, communication module 80, activity sensor 82, and power source 84. Memory 72 includes computer-readable instructions that, when executed by processor 70, cause SD 30 and processor 70 to perform various functions attributed to SD 30 and processor 70 herein (e.g., detection of ventricular dyssynchrony, communication with LPD 16, and/or delivery of anti-tachyarrhythmia shock therapy, if needed). Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof.

Processor 70 controls signal generator 76 to deliver stimulation therapy to heart 12 according to a therapy parameters, which may be stored in memory 72. For example, processor 70 may control signal generator 76 to deliver electrical pulses (e.g., shock pulses) with the amplitudes, pulse widths, frequency, or electrode polarities specified by the therapy parameters. In this manner, signal generator 76 may deliver electrical pulses to heart 12 via electrodes 34, 38, and/or 40. In addition, housing 30 may be configured as an electrode and coupled to signal generator 76 and/or sensing module 78. SD 30 may use any combination of electrodes to deliver anti-tachycardia therapy and/or detect electrical signals from patient 14. However, in general, coil electrode 38 may be used to deliver an anti-tachyarrhythmia shock, if necessary.

Signal generator 76 may also include shock module 75. Shock module 75 may include circuitry and/or capacitors required to deliver an anti-tachyarrhythmia shock. For example, signal generator 76 may charge shock module 75 to prepare for delivering a shock. Shock module 75 may then discharge to enable signal generator 76 to deliver the shock to patient 14 via one or more electrodes. In other examples, shock module 75 may be located within SD 30 but outside of signal generator 76.

Signal generator 76 is electrically coupled to electrodes 34, 38, and 40. In the illustrated example, signal generator 76 is configured to generate and deliver electrical stimuli (e.g. anti-tachyarrhythmia shock therapy) to heart 12. For example, signal generator 76 may, using shock module 75, deliver shocks to heart 12 via a subset of electrodes 34, 38, and 40. In some examples, signal generator 76 may deliver pacing stimulation, and cardioversion or defibrillation shocks in the form of electrical pulses. In other examples, signal generator may deliver one or more of these types of stimulation or shocks in the form of other signals, such as sine waves, square waves, or other substantially continuous time signals.

Signal generator 76 may include a switch module and processor 70 may use the switch module to select, e.g., via a data/address bus, which of the available electrodes are used to deliver shock and/or pacing pulses. The switch module may include a switch array, switch matrix, multiplexer, or any other type of switching device suitable to selectively couple stimulation energy to selected electrodes.

Electrical sensing module 78 may be configured to monitor signals from at least one of electrodes 34, 38, and 40 in order to monitor electrical activity of heart 12, impedance, or other electrical phenomenon. Sensing may be done to determine heart rates or heart rate variability, or to detect arrhythmias (e.g., tachyarrhythmia) or other electrical signals. Sensing module 78 may also include a switch module to select which of the available electrodes are used to sense the heart activity, depending upon which electrode combination, or electrode vector, is used in the current sensing configuration. In examples with several electrodes, processor 70 may select the electrodes that function as sense electrodes, i.e., select the sensing configuration, via the switch module within sensing module 78. Sensing module 78 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 70, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 70 may control the functionality of sensing module 78 by providing signals via a data/address bus.

Processor 70 may include a timing and control module, which may be embodied as hardware, firmware, software, or any combination thereof. The timing and control module may comprise a dedicated hardware circuit, such as an ASIC, separate from other processor 70 components, such as a microprocessor, or a software module executed by a component of processor 70, which may be a microprocessor or ASIC. The timing and control module may implement programmable counters. If SD 30 is configured to generate and deliver pacing pulses to heart 12, such counters may control the basic time intervals associated with DDD, WI, DVI, VDD, AAI, DDI, DDDR, WIR, DVIR, VDDR, AAIR, DDIR and other modes of pacing.

Intervals defined by the timing and control module within processor 70 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 78 for a time interval during and after delivery of electrical stimulation to heart 12. The durations of these intervals may be determined by processor 70 in response to stored data in memory 72. The timing and control module of processor 70 may also determine the amplitude of the cardiac pacing pulses.

Interval counters implemented by the timing and control module of processor 70 may be reset upon sensing of R-waves and P-waves with detection channels of sensing module 78. The value of the count present in the interval counters when reset by sensed R-waves and P-waves may be used by processor 70 to measure the durations of R-R intervals, P-P intervals, P-R intervals and R-P intervals, which are measurements that may be stored in memory 72. In some examples, processor 70 may determine that ventricular dyssynchrony has occurred based on AV interval and P-wave width measurements. Ventricular dyssynchrony is automatically addressed by updating AV delays every minute based on AV interval and P wave width measurements.

In some examples, communication module 80 may be used to detect communication signals from LPD 16. LPD 16 may not include telemetry circuitry. Instead, LPD 16 may generate electrical signals via one or more electrodes with amplitudes and/or patterns representative of information to be sent to SD 30. The electrical signals may be carried by pacing pulses or separate communication signals configured to be detected by SD 30. In this manner, communication module 80 may be configured to monitor signals sensed by sensing module 78 and determine when a communication message is received from LPD 16.

In other examples, SD 30 may also transmit communication messages to LPD 16 using electrical signals from one or more of electrodes 34, 38, and 40. In this case, communication module 80 may be coupled to signal generator 76 to control the parameters of generated electrical signals or pulses. Alternatively, processor 70 may detect communications via sensing module 78 and/or generate communications for deliver via signal generator 76. Although communication module 80 may be used to communicate using electrical signals via electrodes 34, 38 and 40, communication module 80 may alternatively or in addition use wireless protocols such as RF telemetry to communicate with LPD 16 or other medical devices. In some examples, telemetry module 74 may include this wireless communication functionality.

Memory 72 may be configured to store a variety of operational parameters, therapy parameters, sensed and detected data, and any other information related to the monitoring, therapy and treatment of patient 14. Memory 72 may store, for example, thresholds and parameters indicative of cardiac conditions such as ventricular dyssynchrony and/or therapy parameter values that at least partially define delivered CRT such as fusion pacing. In some examples, memory 72 may also store communications transmitted to and/or received from LPD 16.

Activity sensor 82 may be contained within the housing of SD 30 and include one or more accelerometers or other devices capable of detecting motion and/or position of SD 30. For example, activity sensor 82 may include a 3-axis accelerometer that is configured to detect accelerations in any direction in space. Accelerations detected by activity sensor 82 may be used by processor 70 to identify potential noise in signals detected by sensing module 78 and/or confirm the detection of arrhythmias or other patient conditions.

Telemetry module 74 includes any suitable hardware, firmware, software or any combination thereof for communicating with another device, such as programmer 20 (FIG. 1). As described herein, telemetry module 74 may transmit generated or received arrhythmia data, therapy parameter values, communications between SD 30 and LPD 16, or any other information. For example, telemetry module 74 may transmit information representative of sensed physiological data such as R-R intervals or any other data that may be used by LPD 16 to determine a condition of patient 14. Telemetry module 74 may also be used to receive updated therapy parameters from programmer 20. Under the control of processor 70, telemetry module 74 may receive downlink telemetry from and send uplink telemetry to programmer 20 with the aid of an antenna, which may be internal and/or external. Processor 70 may provide the data to be uplinked to programmer 20 and the control signals for the telemetry circuit within telemetry module 74, e.g., via an address/data bus. In some examples, telemetry module 74 may provide received data to processor 70 via a multiplexer. In some examples, SD 30 may signal programmer 20 to further communicate with and pass the alert through a network such as the Medtronic CareLink® Network developed by Medtronic, Inc., of Minneapolis, Minn., or some other network linking patient 14 to a clinician. SD 30 may spontaneously transmit the diagnostic information to the network or in response to an interrogation request from a user.

Power source 84 may be any type of device that is configured to hold a charge to operate the circuitry of SD. Power source 84 may be provided as a rechargeable or non-rechargeable battery. In other examples, power source 84 may also incorporate an energy scavenging system that stores electrical energy from movement of SD 30 within patient 14.

There may be numerous variations to the configuration of SD 30, as described herein. In the examples of FIGS. 2A, 2B, and 4, SD 30 may include housing 32 configured to be implanted in patient 14 external to a rib cage of patient 14, one or more electrodes (e.g., electrodes 34, 38, and 40) configured to be disposed external to the rib cage, and shock module 75 configured to at least partially deliver antitachyarrhythmia shock therapy to patient 14 via the one or more electrodes.

SD 30 may also include communication module 80 configured to transmit and/or receive communication messages between LPD 16 configured to be implanted within heart 12 of patient 14 and a sensing module 78 configured to sense an electrical signal from heart 12 of patient 14 via the one or more electrodes. Further, SD 30 may include one or more processors 70 configured to detect a ventricular dyssynchrony within the sensed electrical signal and determine, based on the detected ventricular dyssynchrony, to deliver CRT to patient 14 to treat the detected ventricular dyssynchrony. Processor 70 may also be configured to transmit, via communication module 80 and prior to delivering CRT, a communication message to LPD 16 requesting LPD 16 deliver fusion pacing to heart 12 of patient 14.

Figure 5:
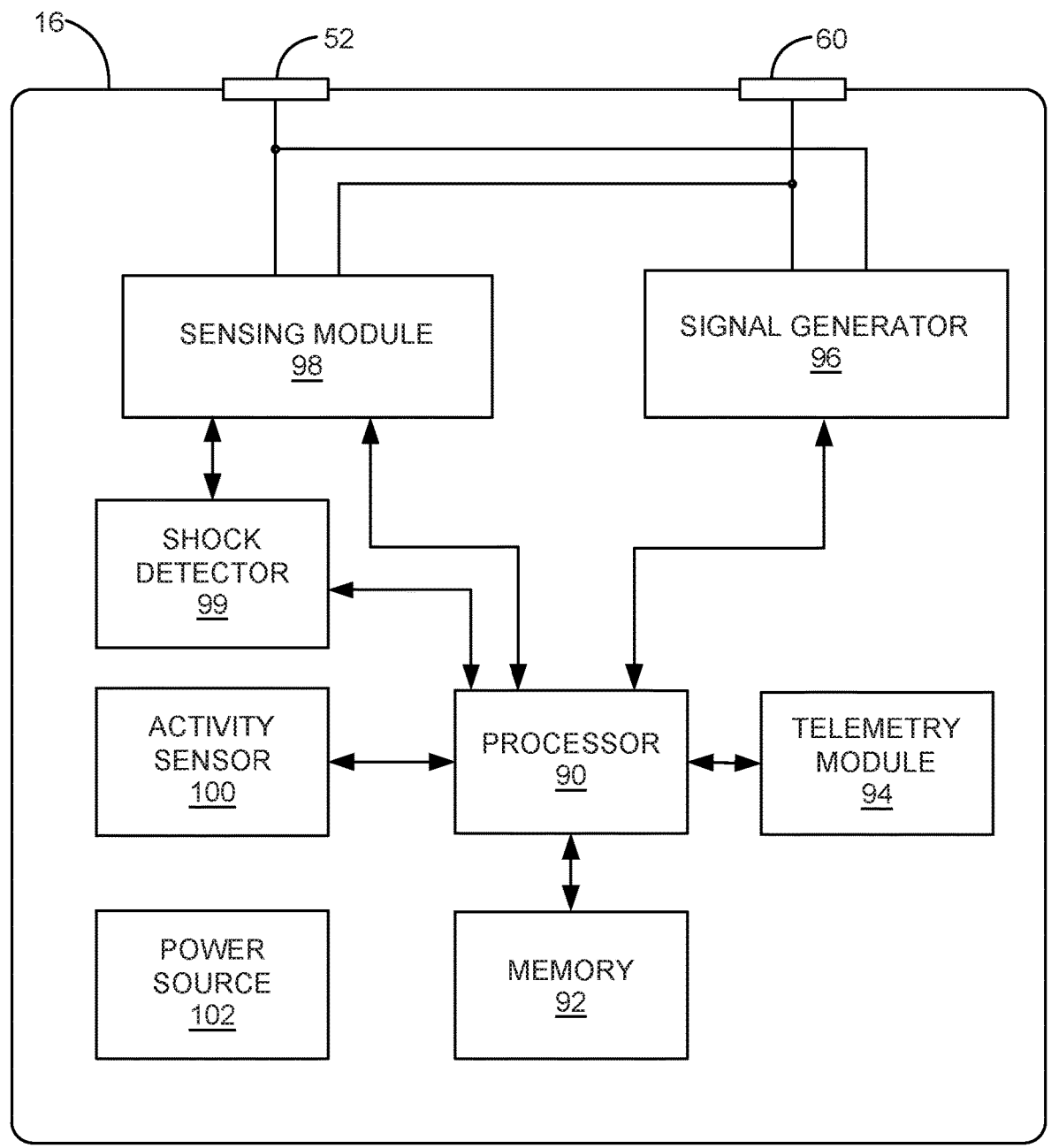
FIG. 5 is a functional block diagram illustrating an example configuration of the LPD of FIG. 1.

FIG. 5 is a functional block diagram illustrating an example configuration of LPD 16 of FIG. 1. In the illustrated example, LPD 16 includes a processor 90, memory 92, signal generator 96, sensing module 98, shock detector 99, activity sensor 100, telemetry module 94, and power source 102. Memory 92 includes computer-readable instructions that, when executed by processor 90, cause LPD 16 and processor 90 to perform various functions attributed to LPD 16 and processor 90 herein (e.g., detecting ventricular dyssynchrony, arrhythmias, communicating with SD 30, and delivering anti-tachycardia pacing and post-shock pacing). Memory 92 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 90 may include any one or more of a microprocessor, a controller, a digital signal processor (DSP), an application specific integrated circuit (ASIC), a field-programmable gate array (FPGA), or equivalent discrete or analog logic circuitry. In some examples, processor 90 may include multiple components, such as any combination of one or more microprocessors, one or more controllers, one or more DSPs, one or more ASICs, or one or more FPGAs, as well as other discrete or integrated logic circuitry. The functions attributed to processor 90 herein may be embodied as software, firmware, hardware or any combination thereof.

Processor 90 controls signal generator 96 to deliver stimulation therapy to heart 12 according to a therapy parameters, which may be stored in memory 92. For example, processor 90 may control signal generator 96 to deliver electrical pulses with the amplitudes, pulse widths, frequency, or electrode polarities specified by the therapy parameters. In this manner, signal generator 96 may deliver pacing pulses (e.g., fusion pacing) to heart 12 via electrodes 52 and 60. Although LPD 16 may only include two electrodes, e.g., electrodes 52 and 60, LPD 16 may utilize three or more electrodes in other examples. LPD 16 may use any combination of electrodes to deliver therapy and/or detect electrical signals from patient 14.

Signal generator 96 is electrically coupled to electrodes 52 and 60 carried on the housing of LPD 16. In the illustrated example, signal generator 96 is configured to generate and deliver electrical stimulation therapy to heart 12. For example, signal generator 96 may deliver pulses to a portion of cardiac muscle within heart 12 via electrodes 52 and 60. In some examples, signal generator 96 may deliver pacing stimulation in the form of electrical pulses. In other examples, signal generator may deliver one or more of these types of stimulation in the form of other signals, such as sine waves, square waves, or other substantially continuous time signals. Although LPD 16 is generally described has delivering pacing pulses, LPD 16 may deliver cardioversion or defibrillation pulses in other examples. Fusion pacing may be delivered to patient 14 as defined by a set of parameters. These parameters may include pulse intervals, pulse width, current and/or voltage amplitudes, and durations for each pacing mode.

Signal generator 96 may also include circuitry for measuring the capture threshold of one or both electrodes 52 and 60. The capture threshold may indicate the voltage necessary to induce depolarization of the surrounding cardiac muscle. For example, signal generator 96 may measure the voltage of pacing signals needed to induce synchronized ventricular contractions. In examples in which LPD 16 includes more than two electrodes, signal generator 96 may include a switch module and processor 90 may use the switch module to select, e.g., via a data/address bus, which of the available electrodes are used to deliver pacing pulses. The switch module may include a switch array, switch matrix, multiplexer, or any other type of switching device suitable to selectively couple stimulation energy to selected electrodes. In the instance that the capture threshold exceeds useable limits, processor 90 may withhold delivery of therapeutic pacing. In addition, processor 90 may transmit communication to SD 30 if pacing cannot be delivered.

Electrical sensing module 98 monitors signals from at least one of electrodes 52 and 60 in order to monitor electrical activity of heart 12, impedance, or other electrical phenomenon. Sensing may be done to determine heart rates or heart rate variability, or to detect ventricular dyssynchrony, arrhythmias (e.g., tachyarrhythmias) or other electrical signals. Sensing module 98 may also include a switch module to select which of the available electrodes (or electrode polarity) are used to sense the heart activity, depending upon which electrode combination, or electrode vector, is used in the current sensing configuration. In examples with several electrodes, processor 90 may select the electrodes that function as sense electrodes, i.e., select the sensing configuration, via the switch module within sensing module 98. Sensing module 98 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 90, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 90 may control the functionality of sensing module 98 by providing signals via a data/address bus.

Processor 90 may include a timing and control module, which may be embodied as hardware, firmware, software, or any combination thereof. The timing and control module may comprise a dedicated hardware circuit, such as an ASIC, separate from other processor 90 components, such as a microprocessor, or a software module executed by a component of processor 90, which may be a microprocessor or ASIC. The timing and control module may implement programmable counters. If LPD 16 is configured to generate and deliver pacing pulses to heart 12, such counters may control the basic time intervals associated with DDD, WI, DVI, VDD, AAI, DDI, DDDR, WIR, DVIR, VDDR, AAIR, DDIR and other modes of pacing. Example LPDs that may deliver pacing using such modes are described in U.S. patent application Ser. No. 13/665,492 to Bonner et al., entitled, "LEADLESS PACEMAKER SYSTEM," and filed on Oct. 31, 2012, or in U.S. patent application Ser. No. 13/665,601 to Bonner et al., entitled, "LEADLESS PACEMAKER SYSTEM," and filed on Oct. 31, 2012. U.S. patent application Ser. No. 13/665,492 to Bonner et al. and U.S. patent Ser. No. 13/665,601 to Bonner et al. are both incorporated herein by reference in their entireties.

In addition to detecting and identifying specific types of cardiac rhythms (types of cardiac events), sensing module 98 may also sample the detected intrinsic signals to generate an electrogram or other time-based indication of cardiac events. Processor 90 may also be able to coordinate the delivery of pacing pulses from different LPDs implanted in different chambers of heart 12, such as an LPD implanted in the other ventricle. For example, processor 90 may identify delivered pulses from other LPDs via sensing module 98 and updating pulse timing. In other examples, LPDs may communicate with each other via telemetry module 94 and/or instructions over a carrier wave (such as a stimulation waveform).

Memory 92 may be configured to store a variety of operational parameters, therapy parameters, sensed and detected data, and any other information related to the therapy and treatment of patient 14. In the example of FIG. 5, memory 92 may store sensed ECGs, detected arrhythmias, communications from SD 30, and therapy parameters. In other examples, memory 92 may act as a temporary buffer for storing data until it can be uploaded to SD 30, another implanted device, or programmer 20.

Activity sensor 100 may be contained within the housing of LPD 16 and include one or more accelerometers or other devices capable of detecting motion and/or position of LPD 16. For example, activity sensor 100 may include a 3-axis accelerometer that is configured to detect accelerations in any direction in space. Specifically, the 3-axis accelerator may be used to detect LPD 16 motion that may be indicative of cardiac events and/or noise. For example, processor 16 may monitor the accelerations from activity sensor 100 to confirm or detect arrhythmias. Since LPD 16 may move with a chamber wall of heart 12, the detected changes in acceleration may also be indicative of contractions. Therefore, LPD 16 may be configured to identify heart rates and confirm ventricular dyssynchrony sensed via sensing module 98.

Telemetry module 94 includes any suitable hardware, firmware, software or any combination thereof for communicating with another device, such as programmer 20 or SD 30 (FIG. 1). Under the control of processor 90, telemetry module 94 may receive downlink telemetry from and send uplink telemetry to programmer 20 with the aid of an antenna, which may be internal and/or external. Processor 90 may provide the data to be uplinked to programmer 20 and the control signals for the telemetry circuit within telemetry module 94, e.g., via an address/data bus. In some examples, telemetry module 94 may provide received data to processor 90 via a multiplexer.

In some examples, LPD 16 may signal programmer 20 to further communicate with and pass the alert through a network such as the Medtronic CareLink® Network developed by Medtronic, Inc., of Minneapolis, Minn., or some other network linking patient 14 to a clinician. LPD 16 may spontaneously transmit information to the network or in response to an interrogation request from a user.

In other examples, processor 90 may be configured to transmit information to another device, such as SD 30 using electrodes 52 and 60. For example, processor 90 may control signal generator 96 to generate electrical signals representative of commands such as the detection of ventricular dyssynchrony, confirmation that ventricular dyssynchrony has been detected, a request to monitor electrical signals for ventricular dyssynchrony, or even signals to "wake up" an SD in a sleep mode. In other examples, processor 90 may cause telemetry module 94 to transmit information representative of sensed physiological data such as R-R intervals or any other data that may be used by SD 30 to determine a condition of patient 14 (e.g., whether or not patient 14 is experiencing ventricular dyssynchrony). The communication may be in the form of dedicated communication signals.

Alternatively, processor 90 may communicate with SD 30 by delivering pacing pulses at specific intervals that would be identifiable by SD 30 as non-physiologic and intended to convey information. In other words, these pulses intended for communication with SD 30. SD 30 may be configured to identify, or distinguish, these pulses from signals indicative of normal or non-normal heart beats, signals indicative of ectopic or non-ectopic heart beats, signals indicative of noise (e.g., skeletal muscle noise), or any other signals indicative of typically physiological or therapeutic electrical signals. The communication pulses may or may not be therapeutic pulses or signals. SD 30 may detect the intervals between these pulses as code for specific messages from LPD 16. For example, the pacing pulses may be varied and/or repeated in certain patterns detectable by SD 30 and still therapeutic. LPD 16 may also be configured to detect such communication messages via electrodes 52 and 60. Processor 90 may monitor sensing module 98 for such communications. Alternatively, LPD 16 may include a communication module, similar to communication module 80 of FIG. 4, to detect any communications received via sensing module 98. In any example, LPD 16 may be configured for one-way communication to or from another device such as SD 30 or two-way communication with another device such as SD 30 using any type of communication protocol.

Power source 102 may be any type of device that is configured to hold a charge to operate the circuitry of LPD 16. Power source 102 may be provided as a rechargeable or non-rechargeable battery. In other example, power source 102 may incorporate an energy scavenging system that stores electrical energy from movement of LPD 16 within patient 14.

There may be numerous variations to the configuration of LPD 16, as described herein. In one example, LPD 16 includes a housing configured to be implanted within heart 12 of patient 14, one or more electrodes (e.g., electrodes 52 and 60) coupled to the housing, fixation mechanism 62 configured to attach the housing to tissue of heart 12, sensing module 98 configured to sense an electrical signal from heart 12 of patient 14 via the one or more electrodes, and signal generator 96 configured to deliver therapy to heart 12 of patient 14 via the one or more electrodes. LPD 16 may also include processor 90 configured to receive a communication message from SD 30 requesting LPD 16 deliver CRT to heart 12, where SD 30 is configured to be implanted exterior to a rib cage of patient 14. Processor 90 may also be configured to determine, based on the sensed electrical signal, whether to deliver CRT to heart 12, and, in response to the determination, command signal generator 96 to deliver the CRT therapy. Processor 90 may also be configured to control signal generator 96 to deliver post-shock pacing to patient 14 in response to shock detector 99 detecting an anti-tachyarrhythmia shock.

Figure 6:
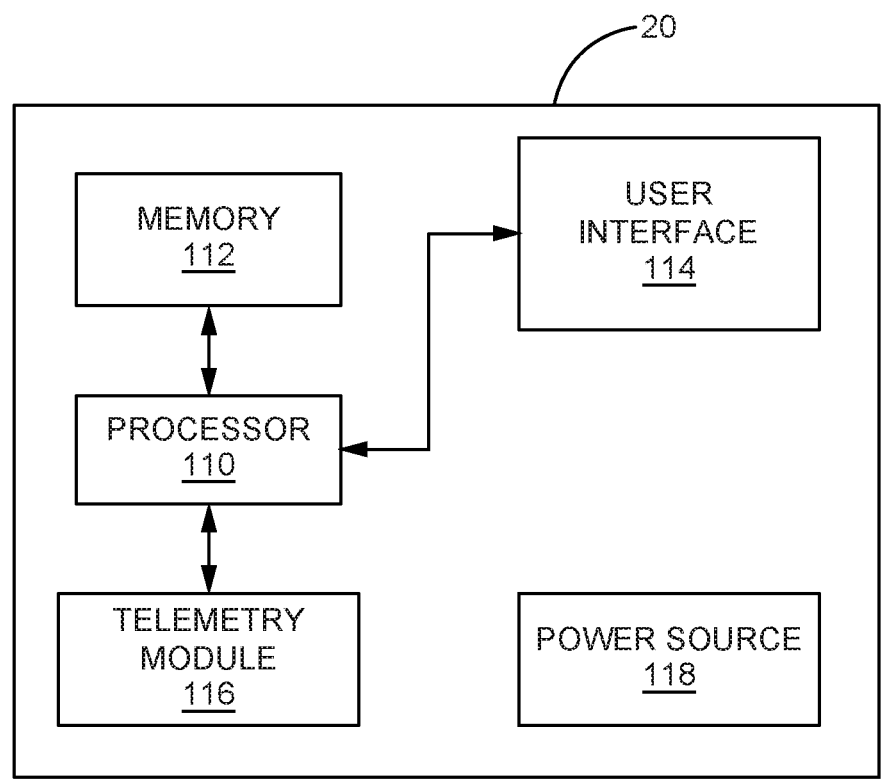
FIG. 6 is a functional block diagram illustrating an example configuration of the programmer of FIG. 1.

FIG. 6 is a functional block diagram illustrating an example configuration of external programmer 20 of FIG. 1. As shown in FIG. 6, programmer 20 may include a processor 110, memory 112, user interface 114, telemetry module 116, and power source 118. Programmer 20 may be a dedicated hardware device with dedicated software for programming of LPD 16 and/or SD 30. Alternatively, programmer 20 may be an off-the-shelf computing device running an application that enables programmer 20 to program LPD 16 and/or SD 30.

A user may use programmer 20 to configure the operational parameters of and retrieve data from LPD 16 and/or SD 30 (FIG. 1). In one example, programmer 20 may communicate directly to both LPD 16 and SD 30. In other examples, programmer may communicate to one of LPD 16 or SD 30, and that device may relay any instructions or information to or from the other device. The clinician may interact with programmer 20 via user interface 114, which may include display to present graphical user interface to a user, and a keypad or another mechanism for receiving input from a user. In addition, the user may receive an alert or notification from SD 30 indicating that a shock has been delivered, any other therapy has been delivered, or any problems or issues related to the treatment of patient 14.

Processor 110 can take the form one or more microprocessors, DSPs, ASICs, FPGAs, programmable logic circuitry, or the like, and the functions attributed to processor 110 herein may be embodied as hardware, firmware, software or any combination thereof. Memory 112 may store instructions that cause processor 110 to provide the functionality ascribed to programmer 20 herein, and information used by processor 110 to provide the functionality ascribed to programmer 20 herein. Memory 112 may include any fixed or removable magnetic, optical, or electrical media, such as RAM, ROM, CD-ROM, hard or floppy magnetic disks, EEPROM, or the like. Memory 112 may also include a removable memory portion that may be used to provide memory updates or increases in memory capacities. A removable memory may also allow patient data to be easily transferred to another computing device, or to be removed before programmer 20 is used to program therapy for another patient.

Programmer 20 may communicate wirelessly with LPD 16 and/or SD 30, such as using RF communication or proximal inductive interaction. This wireless communication is possible through the use of telemetry module 116, which may be coupled to an internal antenna or an external antenna. An external antenna that is coupled to programmer 20 may correspond to the programming head that may be placed over heart 12 or the location of the intend implant, as described above with reference to FIG. 1. Telemetry module 116 may be similar to telemetry modules 74 and 94 of respective FIGS. 4 and 5.

Telemetry module 116 may also be configured to communicate with another computing device via wireless communication techniques, or direct communication through a wired connection. Examples of local wireless communication techniques that may be employed to facilitate communication between programmer 20 and another computing device include RF communication according to the 802.11 or Bluetooth specification sets, infrared communication, e.g., according to the IrDA standard, or other standard or proprietary telemetry protocols. An additional computing device in communication with programmer 20 may be a networked device such as a server capable of processing information retrieved from LPD 16. In other examples, LPD 16 may not use a shock detector to time the beginning or ending of post-shock pacing. Instead, LPD 16 may determine when to deliver post-shock pacing based on a command from SD 30. For example, SD 30 may determine that a shock will be delivered and transmit a shock imminent command to LPD 16. In response to receiving the shock imminent command, LPD 16 may enter a shock state for a predetermined period of time. This predetermined period of time may be stored in memory 92 or sent along with the shock imminent command from SD 30. The predetermined period of time may have a sufficient duration such that any shock would be delivered prior to the predetermined period expiring. In response to the predetermined period elapsing, LPD 16 may exit the shock state and enter a post-shock pacing state in which LPD 16 delivers post-shock pacing and/or first determines whether post-shock pacing is needed.

Measurement of activation times can be performed by picking an appropriate fiducial point (e.g., peak or maximum values, trough or minimum values, minimum positive or negative slopes, maximum positive or negative slopes, zero crossings, threshold crossings, etc. of a near or far-field electrograms) and measuring a time period between the delivery of pacing stimulus using a pacing electrode and the appropriate fiducial point within the electrical activity (e.g., EGM) sensed by a non-pacing electrode. In other words, activation times between a pacing electrode and a non-pacing electrode distant from the pacing electrode may be measured by picking, or selecting, an appropriate point within the EGM recorded by the non-pacing electrode during pacing therapy (e.g., biventricular stimulation, LV-only pacing, RV-only pacing, etc.) with respect to the pacing spike. Exemplary activation times shown within different waveforms, or EGMs 200, will be further shown and described herein with respect to FIG. 9. The set of electrograms 200 comprise electrograms 202, 204, 206.

Figure 9:
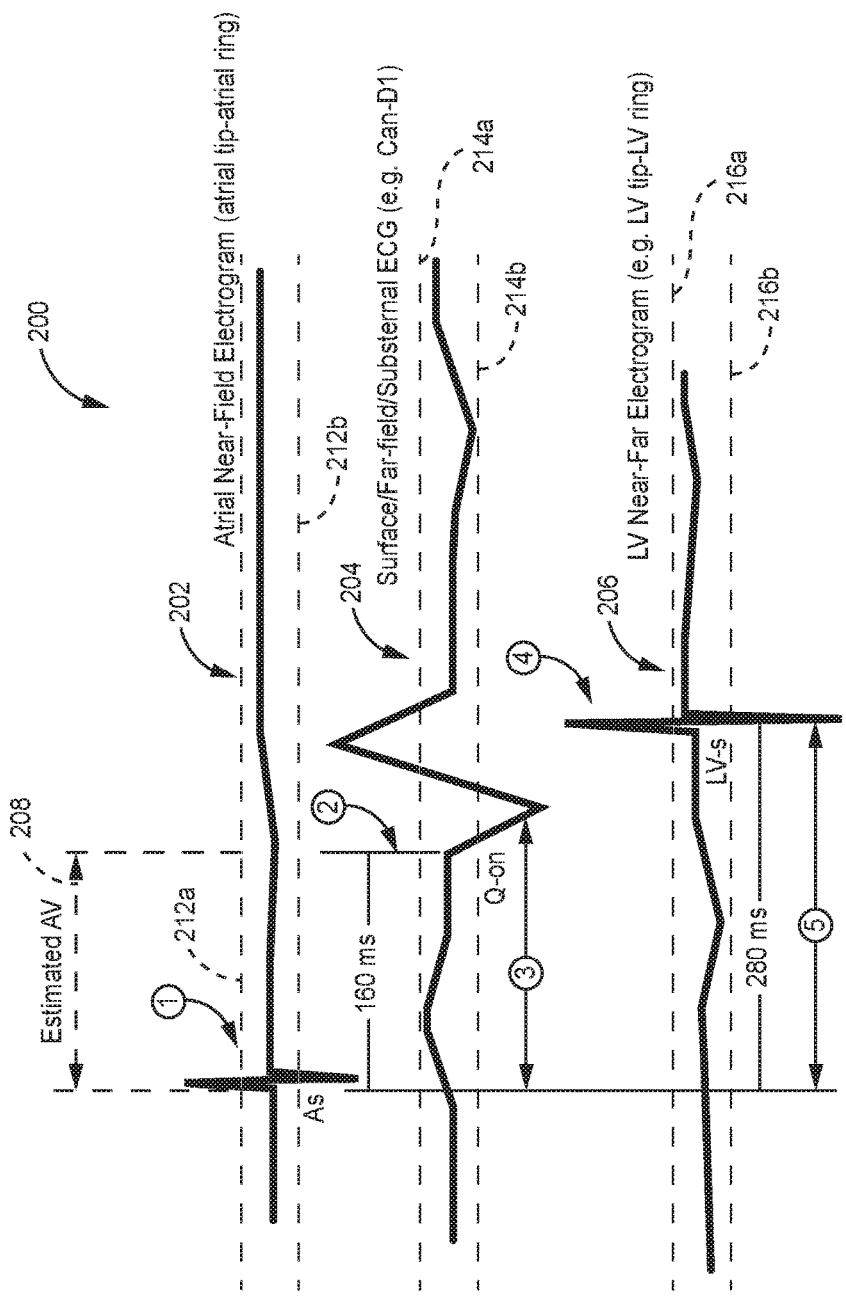
FIG. 9 depicts a set of exemplary electrograms and right ventricular activation time calculations.

Exemplary electrograms 202, 204, 206, were generated to show local activity (202, 206) in the atrium and left ventricle, respectively, while global activation (204) depicts different heart waves. The first nearfield EGM 202 displays local activation in the atrium. The P-wave (denoted as 1 on FIG. 9) is obtained using electrodes in the atrium. For example, the atrial tip to atrial ring on the right atrial lead can be used to sense the P-wave. An example of atrial tip to atrial ring on the right atrial lead is shown and described relative to U.S. patent application Ser. No. 15/222,461 and is incorporated by reference in its entirety herein to show a conventional pacing configuration that could be used without a RV lead to estimate a pacing delay (e.g. AV delay). The global activation of the heart, electrogram 204, is obtained using farfield electrodes and shows Qon (denoted as 3 on FIG. 9). Exemplary farfield electrodes can be obtained from a variety of sources. For example, farfield electrodes can include an electrode on the can or housing of the implantable medical device to the D1 electrode associated with the substernal lead. In another embodiment, surface electrodes (e.g. ECG belt etc.) can be used to obtained global activation of the heart. The R wave is denoted as 4 on FIG. 9. The AV delay, denoted as 5 on FIG. 9, is 280 ms. Electrogram 206 is a bipolar, near-far electrogram using a LV tip electrode and LV ring electrode on the LV lead to capture near-field LV activity. The peak value of the near-field electrogram 206 corresponds to the time of local LV electrical activation and provides an estimate of the time of local left ventricular sensing of electrical activity. The exemplary methods and/or devices described herein may track, or monitor, ventricular activation times (e.g., right ventricular activation time, left ventricular activation time, etc.) and adjust one or more pacing parameters such as AV delay based on the monitored activation times. One manifestation of the basic flow can be seen in exemplary method 300 of FIG. 5. Exemplary method 300 includes various processes to measure ventricular activation times and to modify AV delays for use in delivering pacing therapy based on the measured ventricular activation times. Exemplary method 300 is intended to illustrate the general functional operation of the devices described herein and should not be construed as reflective of a specific form of software or hardware necessary to practice all of the methods described herein. It is believed that the particular form of software will be determined primarily by the particular system architecture employed in the device (e.g., IMD (e.g. (SD 30 and/or LPD16)) and by the particular detection and therapy delivery methodologies employed by the device and/or system. Providing software and/or hardware to accomplish the described methods in the context of any modern IMD, given the disclosure herein, is within the abilities of one of skill in the art.

The exemplary method 300 of FIG. 5 includes delivering pacing therapy 102 (e.g., using the IMD 16 described herein). Delivering pacing therapy 102 may include monitoring a patient's heart and delivering electrical pacing pulses to the patient's heart, e.g., to maintain the patient's heartbeat (e.g., to regulate a patient's heartbeat, to improve and/or maintain a patient's hemodynamic efficiency, etc.). More specifically, the pacing therapy 102 may include LV-only pacing or RV-only pacing. In other words, pacing therapy may be delivered to either the left ventricle or the right ventricle of the patient's heart. As described herein, the delivery of pacing therapy may be based on one or more pacing parameters including an AV delay, which may be modified according to exemplary method 300.

During the delivery of pacing therapy, the pacing therapy may become less effective due to, e.g., changes in the patient's physical activity, changes in cardiac tissue, changes in ventricular conduction velocity, changes in ventricular conduction patterns, changes in intrinsic conduction AV times, changes in heart rate, changes in sympathetic or parasympathetic stimulation, etc. To compensate for such changes, the exemplary method 300 may sense electrical activity of the patient's heart during the delivery of pacing therapy with one or more electrodes not used to pace the patient's heart. For example, the electrical activity may be sensed, or monitored, using at least one sensing electrode during the delivery of pacing stimulus (e.g., pacing pulses) from one or more pacing electrodes such that the electrical activity which results from the pacing stimulus or an intrinsic conduction (e.g., whichever occurs first and results in a depolarization) may be sensed, or seen, in the electrogram of the at least one sensing electrode (e.g., unipolar or bipolar configurations).

More specifically, ventricular activation times may be measured using the sensed electrical activity during the delivery of pacing therapy. In at least one embodiment, the pacing therapy may be LV-only pacing therapy, which includes pacing stimulus delivered to only the left ventricle of the patient's heart (and not the right ventricle). As such, the exemplary method delivering LV-only pacing therapy may measure the right ventricular activation time, which is the time between the delivery of pacing stimulus to the left ventricle and the depolarization of the right ventricle due to, e.g., an intrinsic conduction or the pacing stimulus delivered to the left ventricle and conducted to the right ventricle (e.g., whichever occurs first).

In at least another embodiment, the pacing therapy may be RV-only pacing therapy, which includes pacing stimulus delivered to only the right ventricle of the patient's heart (and not the left ventricle). As such, the exemplary method delivering RV-only pacing therapy may measure the left ventricular activation time, which is the time between the delivery of pacing stimulus to the right ventricle and the depolarization of the left ventricle due to, e.g., an intrinsic conduction or the pacing stimulus to the right ventricle (whichever occurs first).

The electrodes used to deliver pacing stimulus and sensing electrical activity for use in measuring activation times may be described in terms of a first electrode and a second electrode. For example, the pacing therapy may be delivered with at least a first electrode and the electrical activity may be sensed with at least a second electrode. The second electrode, or any other electrode configured to sense the electrical activity during the delivery of pacing stimulus, may not be a pacing electrode. In other words, the second electrode may not be configured for delivering pacing therapy. Further, the second, or sensing, electrode may be a pacing electrode that is simply not being used to deliver pacing therapy (e.g., not ever used for delivery of pacing therapy, not being used to deliver pacing therapy at the same time as the first electrode, etc.).

In the example of LV-only pacing therapy, the first electrode, or the pacing electrode, may be configured to pace the left ventricle of patient's heart and the second electrode, or the sensing electrode, may be configured to sense electrical activity of the right ventricle of patient's heart. In at least one LV-only pacing therapy embodiment, the pacing electrode, or first electrode, may be a LV tip electrode configured to pace the free wall of the left ventricle, and the sensing electrode, or second electrode, may be a RV ring electrode, a RV tip electrode, or a RV elongated (e.g., defibrillation) electrode. For example, a near-field right ventricular EGM may be measured, or sensed, between a RV tip electrode and a RV ring electrode. Further, for example, a far-field right ventricular EGM may be measured, or sensed, between a RV tip electrode and a can, or housing, electrode (e.g., electrode 58).

In the example of RV-only pacing therapy, the first electrode, or the pacing electrode, may be configured to pace the right ventricle of patient's heart and the second electrode, or the sensing electrode, may be configured to sense electrical activity of the left ventricle of patient's heart. In at least one RV-only pacing therapy embodiment, the pacing electrode, or first electrode, may be a RV tip electrode configured to pace the endocardial apical or septal wall of the right ventricle, and the sensing electrode, or second electrode, may be a LV ring electrode, a LV tip electrode, or a LV elongated (e.g., defibrillation) electrode. For example, a near-field left ventricular EGM may be measured, or sensed, between a LV tip electrode and a LV ring electrode. Further, for example, a far-field left ventricular EGM may be measured, or sensed, between a LV tip electrode and a can, or housing, electrode (e.g., electrode 58).

Further, the second electrode may be located a distance away from the first electrode (e.g., the pacing electrode) such that an activation time may be monitored. For example, if the first electrode and the second electrode were located too close to one another, an activation time may be too short for use in modifying one more pacing parameters such as, e.g., AV delay.

Since the exemplary method 300 may not use pacing electrodes to sense the electrical activity for use in modifying one or more pacing parameters such as AV delay, sensing 104 may take place for every paced beat (e.g., beat-to-beat, etc.) such that pacing therapy is not interrupted. As such, the ventricular activation time for each heartbeat of a plurality of heartbeats may be monitored using exemplary method 300 without interruption.

As described herein, ventricular activation times may be measured 106 using the electrical activity sensed 104 using one or more sensing electrodes. For example, a fiducial point on the waveform of the sensed electrical activity may be selected to be used with the exemplary method 300. The time between the delivery of the pacing therapy (e.g., to the LV, to the RV, etc.) and the selected fiducial point within the waveform of the sensed electrical activity resulting from either the pacing therapy (e.g., pacing stimulus) or an intrinsic activation is the measured ventricular activation time.

The fiducial point may be selected to be a characteristic of the sensed electrical activity resulting from (e.g., a product of) the pacing therapy or an intrinsic activation that is repeatedly, or consistently, recognizable such that ventricular activation times may be repeatedly, or consistently, measured. In at least one embodiment, the fiducial point may be a peak, or maximum, value in a near-field waveform, or electrogram, sensed by the sensing electrode (e.g., as shown by electrogram 206 shown in FIG. 9). In at least another embodiment, the fiducial point may be a peak, or maximum, negative slope value (e.g., the steepest negative slope) in a far-field waveform, or electrogram, sensed by the sensing electrode (e.g., as shown by electrogram shown in FIG. 9). For example, a derivative function of the far-field electrogram may be calculated, or computed, to determine the peak, or maximum, negative slope value of the far-field electrogram.

Figure 8:
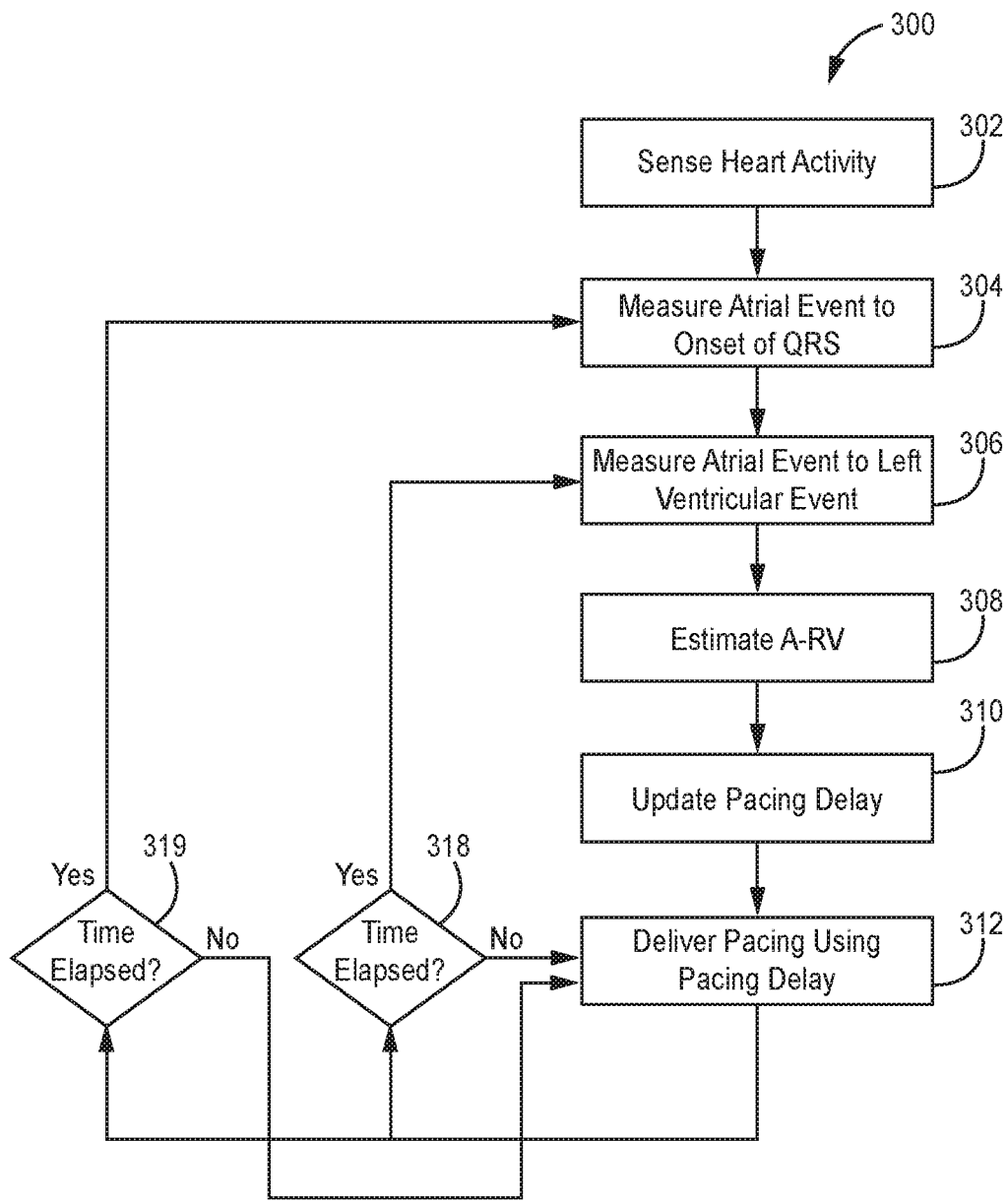
FIG. 8 is a flow chart of an exemplary method for modifying atrioventricular (AV) delay based on estimating right ventricular (RV) timings from left ventricular (LV) sensing times for adaptive CRT using DDD/VDD LV pacing e.g., using the IMDs of FIGS. 1-3 without a right ventricular lead.

Based on the measured activation times, the exemplary method 300 may modify an AV delay, e.g., which may be used in the delivery of pacing therapy, based on the measured activation times. As shown in FIG. 8, before the exemplary method 300 may modify the AV delay, the exemplary method 300 may evaluate one or more of the measured activation times to determine whether the AV delay should be modified. For example, one or more measured activation time may be compared to a predetermined reference activation time indicative of effective, or optimal, pacing therapy. If the one or more activation times are greater than or less than the predetermined reference activation time by a selected threshold value, then exemplary method 300 may modify the AV delay.

The predetermined reference activation time may be defined as an optimal value of the ventricular activation time that produces a maximum stroke volume for a fixed heart rate or the maximum cardiac output for a sinus node driven heart rate or provides effective hemodynamic performance as measured by any number of invasive or noninvasive methods, including sensor-based measurements, narrowest QRS duration on the surface ECG, etc. In at least one embodiment, the predetermined reference activation time may be determined by a mapping function implemented within an implantable medical device which may determine the optimal value based on assessment of patient's intrinsic AV conduction at rest.

The predetermined reference activation time may be established by any number of methods. In at least one embodiment, a mean value representative of a plurality of monitored ventricular activation times, and its variability, may be evaluated for a selected number of beats (e.g., 60 heartbeats) during a post-implant follow-up at physician's office. A physician, or another practitioner, may visually monitor the pacing therapy using, e.g., an electrocardiogram of the patient's heart, to confirm that the pacing therapy is effective. Then, for example, the mean value (or any other statistic) of the monitored ventricular activation times may be calculated and used as the predetermined reference activation time indicative of effective pacing therapy. The variability may be used to calculate a threshold value, which is the difference from the reference activation time that may be acceptable or allowable without indicating ineffective pacing therapy (which may initiate an AV delay adjustment).

In at least one embodiment, a reference activation time for LV-only pacing may be about 50 milliseconds (ms) and the threshold may be about 10 ms. In other words, in this embodiment, if the measured activation time is between about 40 ms (i.e., 50 ms minus 10 ms) and about 60 ms (i.e., 50 ms plus 10 ms), then the measured activation time may be determined to provide effective (e.g., optimal) pacing therapy, and thus, no modification of the AV delay should occur. Such values may be different for each patient and each different electrode combination used for pacing and sensing.

The predetermined reference activation time may be greater than or equal to about 30 ms, about 35 ms, about 40 ms, about 50 ms, about 55 ms, etc. Further, the predetermined reference activation time may be less than or equal to about 60 ms, about 65 ms, about 70 ms, about 80 ms, etc. The threshold value may be greater than or equal to about 2 ms, about 3 ms, about 5 ms, about 7 ms, etc. Further, the threshold value may be less than or equal to about 10 ms, about 12 ms, about 15 ms, 17 ms, etc.

In at least one embodiment, a single measured ventricular activation time may be evaluated to initiate, or trigger, the modification of an AV delay. For example, if the last measured ventricular activation time is greater than or less than a predetermined reference activation time by a selected threshold value, then it may be determined that the AV delay should be modified.

In other embodiments, more than one measured ventricular activation time may be evaluated to initiate the modification of an AV delay. For example, if a first selected number (e.g., 5, 10, etc.) of consecutive measured ventricular activation times are greater than or less than a predetermined reference activation time by a selected threshold value over a second selected number (e.g., 10, 20, etc.) of heartbeats, then it may be determined that the AV delay should be modified. An exemplary method including a determination process based on more than one measured activation time to modify an AV delay is further described herein.

Still further, the standard deviation of one or more measured ventricular activation times may be compared to a selected variability threshold value to determine if the AV delay should be modified. For example, if the standard deviation of a first selected number (e.g., 5) of the activation time differences (e.g., an activation time difference may be the measured ventricular activation time minus the predetermined reference activation time) are less than a selected variability threshold (e.g., 15 ms) over a second selected number of heartbeats (e.g., 10 heartbeats), then it may be determined that the AV delay should be modified. An exemplary method including a determination process based on the standard deviation of one or more measured ventricular activation times to modify an AV delay is further described herein. Although standard deviation is used in this example to evaluate variability, any statistical metric may be used to evaluate the measured activation times. For example, the mean of absolute deviations of each activation time from the mean activation time may be used to evaluate the measured activation times.

If it is determined the AV delay should not be adjusted or modified, the exemplary method 300 may continue delivering pacing therapy, sensing electrical activity, measuring ventricular activation times, and evaluating the activation times to determine whether AV delay or any other pacing parameter (e.g., W delay, modulation of multisite pacing such as pacing from more than one site in the LV or RV, etc.) should be adjusted. If it is determined that AV delay should be adjusted or modified, the exemplary method 300 may advance to modifying the AV delay.

Generally, to modify the AV delay, the AV delay may be shortened or lengthened based upon the monitored ventricular activation times. For example, in LV-only pacing (e.g., in patients with left bundle branch block), if the ventricular activation times (e.g., the time period between the LV pace and the RV activation such as RV activation time shown in FIG. 9) increase during subsequent fusion resynchronization pacing (e.g., RV activation occurs after LV pacing, moving toward a right bundle branch block pattern of activation), the AV delay for the LV pacing may be lengthened, or adjusted to longer values, to maintain ideal fusion. Conversely, in LV-only pacing, if the ventricular activation times subsequently decrease or become negative (e.g., RV activation can occur before LV pacing, moving toward a left bundle branch block pattern of activation), the AV delay for pacing may be shortened, or adjusted to shorter values, to maintain ideal fusion.

Further, when modifying the AV delay, either the last used AV delay or one or more statistical variations of one or more previously used AV delays may be used as a starting point for modification. In at least one embodiment, the AV delay may be set to the last used AV delay plus the last measured activation time minus the predetermined reference activation time.

In one or more embodiments, a mode, median, or average of a selected number of previous AV delays (e.g., the last five AV different delays, the AV delays used for the last 5 heartbeats, 10 heartbeats, 15 heartbeats, 20 heartbeats, etc.) may be used to modify the AV delay. For example, the AV delay may be set to one of a mode, a median, or average of a selected number (e.g., 5, 10 etc.) of previous AV delays plus one of a mode, a median, or average of the selected number of activation time differences. As described herein, an activation time difference may be the measured ventricular activation time minus the predetermined reference activation time.

Another exemplary method for use in modifying AV delay based on monitored ventricular activation. The exemplary method is configured to deliver LV-only pacing therapy. As such, the ventricular activation times measured in are the right ventricular activation times since the left ventricle is being paced. In other words, the measured activation time is the time period between the delivery of a left ventricular pace and the depolarization of the right ventricle due to, e.g., either the pacing stimulus to the left ventricle or an intrinsic conduction.

For each paced heartbeat, a measured activation time, or $\Delta T$, may be measured and calculated continuously or periodically for a selected number of, or N, heartbeats (e.g., 10 successive heartbeats). The measured activation time, or $\Delta T$, is equal to the time between an atrial sense or atrial pace and the right ventricular activation (e.g., as determined by analysis of an electrogram of the right ventricle) minus the AV delay (e.g., the time between either an atrial sense or atrial pace and the left ventricular pace).

The measured activation times may then be evaluated. For example, if the measured activation time, or $\Delta T$, is less than (e.g., less than or equal to) a predetermined reference activation time, or $\Delta Tref$, by a selected threshold value or is greater than (e.g., greater than or equal to) the predetermined reference activation time, or $\Delta Tref$, by the selected threshold, then it may be determined that the AV delay should be adjusted.

As shown, the determination process may also evaluate any statistical metric of the measured activation times such as, e.g., the standard deviation of the measured activation times from the predetermined reference activation times. For example, if a standard deviation of the difference between the measured activation time, or $\Delta T$, and the predetermined reference activation time, or $\Delta Tref$, is less than a variability limit (e.g., 15 ms) for a first selected number of, or M, beats (e.g., 5 heartbeats) out a second selected number of, or N, beats (e.g., 10 heartbeats), then it may be determined that the AV delay should be adjusted. If it is not determined that AV delay should be adjusted in process, the exemplary method may continue delivering LV pacing without adjusting the AV delay.

If it is determined that the AV delay should be adjusted, then the AV delay (e.g., the time period between the atrial sense or atrial pace and the ventricular pace) may be adjusted for the next beat. For example, the AV delay may be set to the median or modal value of the AV delay of a selected number of, or M, heartbeats (e.g., 5 heartbeats) plus a median or modal value of the difference between the measured activation times, or $\Delta T$, and the predetermined reference activation time, or $\Delta Tref$, of the selected number of, or M, heartbeats.

After the AV delay has been adjusted, the exemplary method may evaluate the newly adjusted AV delay to, e.g., determine if the AV delay has been adjusted too far to deliver effective pacing therapy. For example, if the AV delay for pacing reaches an upper limit, the LV-only fusion pacing may be replaced by biventricular pacing at a short-predetermined AV delay. The short-predetermined AV delay may be about 80 ms to about 200 ms. If the AV delay has not exceeded a predetermined upper limit value, then exemplary method may continue delivering LV-only pacing, e.g., using the adjusted AV delay, monitoring ventricular activations times, and evaluating the measured ventricular activation times. Further, although exemplary method is shown for LV-only pacing, it may also be used for patients with right bundle branch block by pacing RV-only and sensing left ventricle activation to determine the AV delay for RV pacing.

Figure 7B:
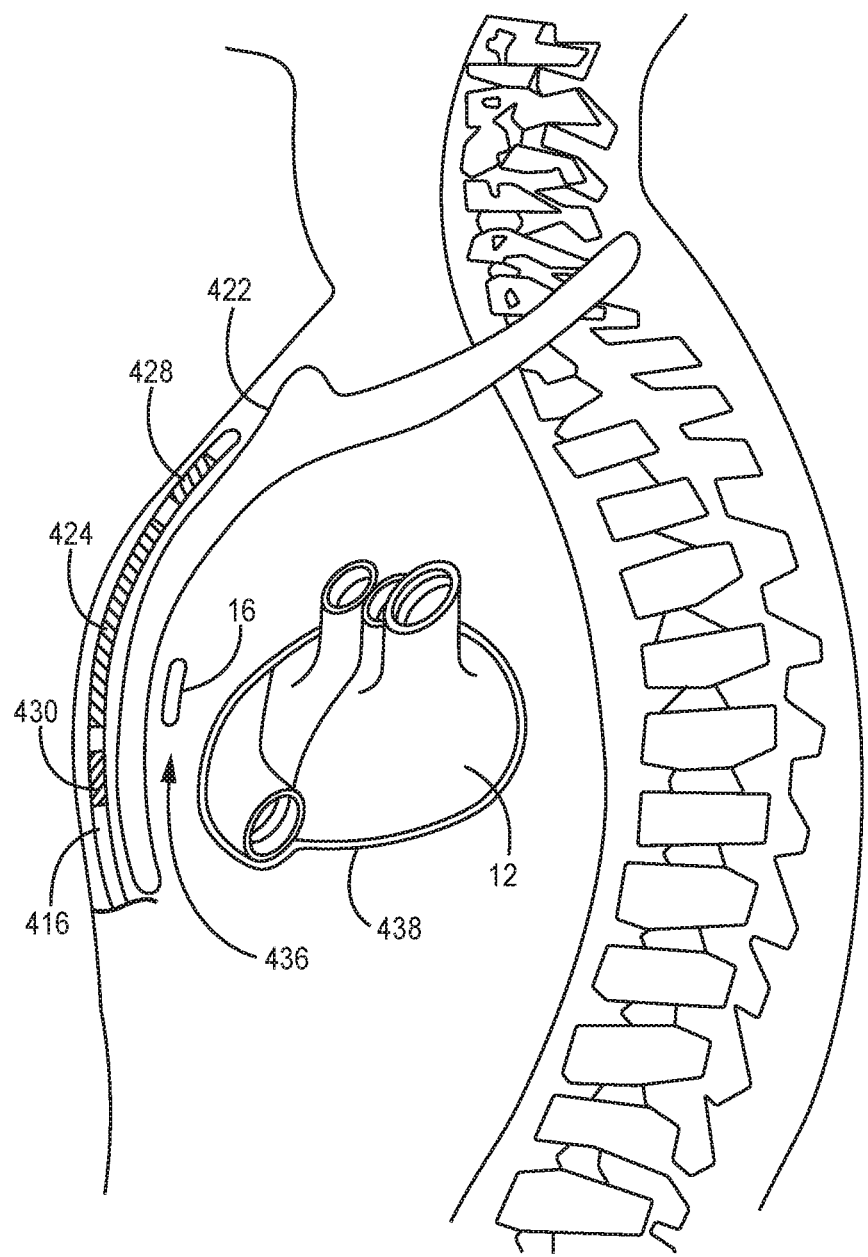
FIG. 7B is a side view of the patient implanted with the extracardiovascular ICD system implanted intra-thoracically.
Figure 7C:
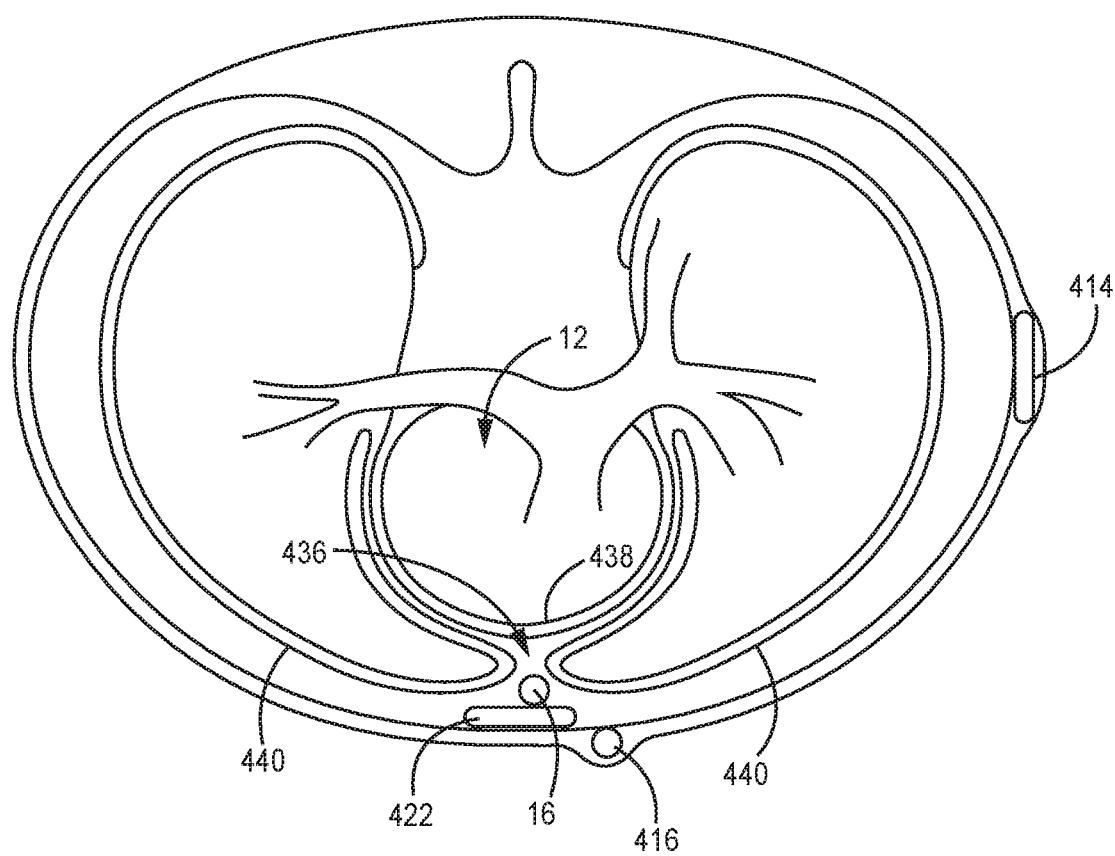
FIG. 7C is a transverse view of the patient implanted with the extracardiovascular ICD system implanted intra-thoracically.
Figure 7D:
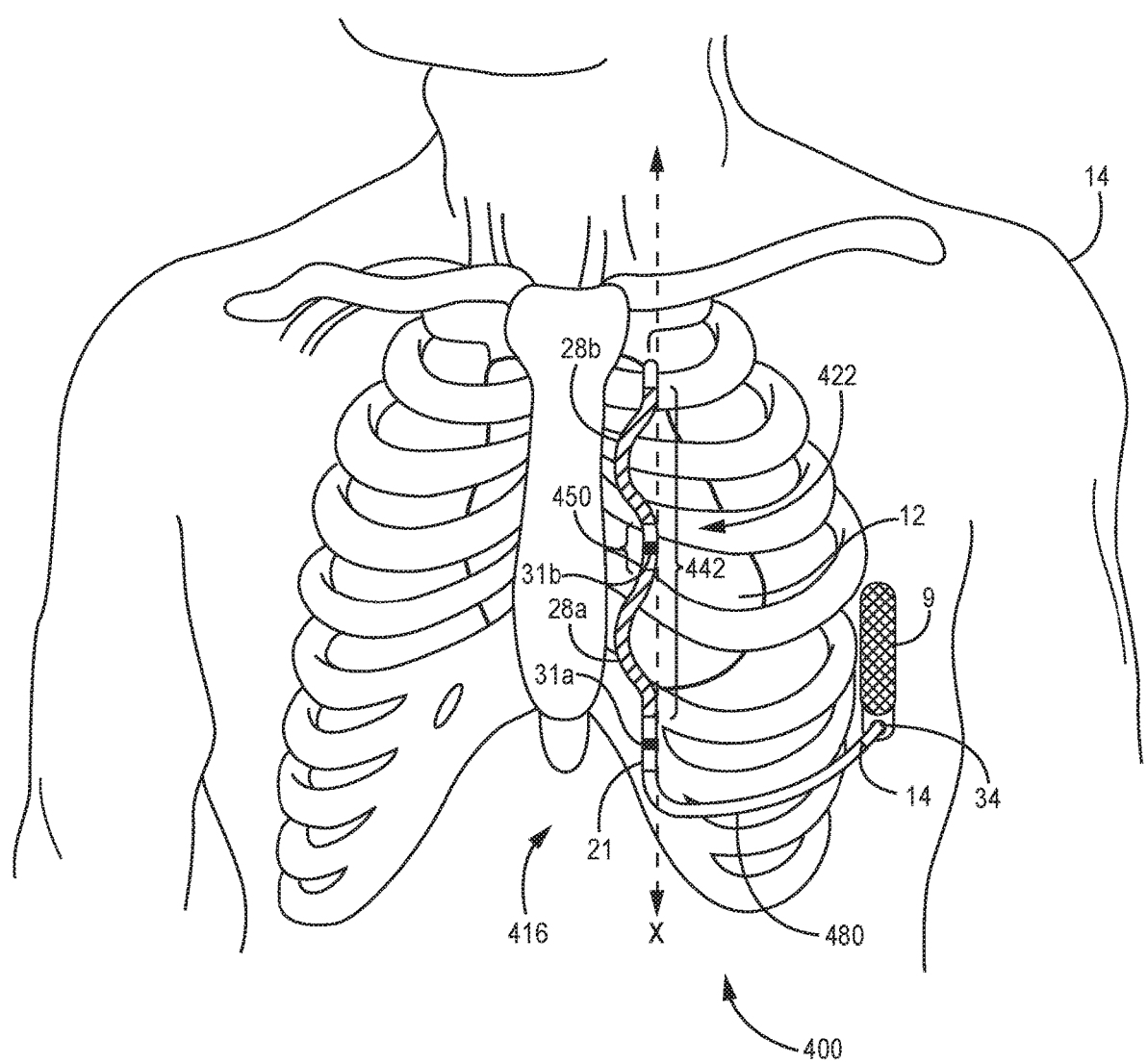
FIG. 7D is a front view of a patient implanted with a similar extracardiovascular ICD system of FIG. 7A implanted intra-thoracically except an undulating medical electrical lead and differently shaped implantable medical device are employed.

FIGS. 7A-C are conceptual diagrams of a patient 14 implanted with an exemplary implantable cardiac system 400 that includes a substernal/retrosternal LPD 16 in order to deliver CRT (e.g. fusion pacing, biventricular pacing or adaptive CRT (i.e. switching between biventricular pacing and fusion pacing). Implantable cardiac system 400 can implement method 300 as described herein. FIG. 7A is a front view of patient 14 implanted with implantable cardiac system 400. FIG. 7B is a side view patient 14 with implantable cardiac system 400. FIG. 7C is a transverse view of patient 14 with implantable cardiac system 400. Implantable cardiac system 400 includes an implantable medical device (IMD) 414 such as an implantable cardiac defibrillator (ICD) or pacemaker connected to a medical electrical lead 416. An exemplary substernal lead is shown and described in US20160158567A, entitled EXTRAVASCULAR IMPLANTABLE ELECTRICAL LEAD HAVING UNDULATING CONFIGURATION, filed Dec. 9, 2015, US20160158567, incorporated by reference in their entirety herein. In the example illustrated in FIGS. 7A-C, IMD 414 is implanted subcutaneously on the left midaxiallary of patient 14. IMD 414 may, however, be implanted at other subcutaneous locations on patient 14 as described herein.

Defibrillation lead 416 includes a proximal end that is connected to IMD 414 and a distal end that includes one or more electrodes. Defibrillation lead 416 extends subcutaneously from IMD 414 toward xiphoid process 20. At a location near xiphoid process 20 defibrillation lead 16 bends or turns and extends subcutaneously superiorily, substantially parallel to sternum 422. The distal end of defibrillation lead 416 may be positioned near the second or third rib of patient 14. However, the distal end of defibrillation lead 416 may be positioned further superior or inferior depending on the location of IMD 414 and other factors. Although illustrated as being offset laterally from and extending substantially parallel to sternum 422 in the example of FIGS. 7A-C, defibrillation lead 416 may be implanted over sternum 422, offset from sternum 422, but not parallel to sternum 422 (e.g., angled lateral from sternum 422 at either the proximal or distal end).

Defibrillation lead 416 includes a defibrillation electrode 424 (D1), which may be an elongated coil electrode, toward the distal end of defibrillation lead 416. Defibrillation lead 416 is placed such that a therapy vector between defibrillation electrode 424 (D2) and a housing or can electrode of IMD 414 is substantially across the ventricle of heart 12.

Defibrillation lead 416 may also include sensing and/or pacing electrodes 428 and 430 located toward the distal end of defibrillation lead 416. In the example illustrated in FIGS. 7A-C, sensing electrodes (S1, S2 respectively) 428 and 430 are separated from one another by defibrillation electrode 424. IMD 414 may sense electrical activity of heart 26 via a combination of sensing vectors that include combinations of electrodes 428 and 430 and the housing or can electrode of IMD 414. For example, IMD 414 may obtain electrical signals sensed using a sensing vector between electrodes 428 and 430, obtain electrical signals sensed using a sensing vector between electrode 428 and the conductive housing or can electrode of IMD 414, obtain electrical signals sensed using a sensing vector between electrode 430 and the conductive housing or can electrode of IMD 414, or a combination thereof. In some instances, IMD 414 may even sense cardiac electrical signals using a sensing vector that includes defibrillation electrode 424.

ICD 414 may analyze the sensed electrical signals from one or more of the sensing vectors of defibrillation lead 416 to detect ventricular dyssynchrony and/or other cardiac conditions (e.g. tachycardia, fibrillation). In response to detecting the ventricular dyssynchrony, IMD 414 may communicate with LPD 16 to initiate fusion pacing or biventricular pacing in an attempt to terminate the ventricular dyssynchrony. The means of communication between LPD 16 and IMD 414 is the same or similar as that which is described herein.

LPD 16 is implanted substernally/retrosternally and communicatively coupled to IMD device 414. LPD 16 and IMD device 414 may, for example, both include a communication module via which the devices exchange wireless communications. LPD 16 and IMD device 414 may, for example, be coupled via inductive coupling, RF coupling, tissue conductance communication, or other wireless communication mechanism.

As indicated above, LPD 16 is implanted substernally/retrosternally, e.g., in the substernal/retrosternal space underneath the sternum but not within the pericardial space or the pleural space. In one example, LPD 16 may be placed in the mediastinum 436 and, more particularly, in the anterior mediastinum. The anterior mediastinum is bounded laterally by pleurae 440, posteriorly by pericardium 438, and anteriorly by sternum 22. LPD 16 may be implanted within the mediastinum such that the one or more electrodes of LPD 16 are located over a cardiac silhouette of the ventricle as observed via fluoroscopy. In the example illustrated in FIGS. 7A-C, LPD 16 is located substantially centered under sternum 422. In other instances, however, LPD 16 may be implanted such that it is offset laterally from the center of sternum.

Although described herein as being implanted in the substernal/retrosternal space, the mediastinum, or the anterior mediastinum, LPD 16 may be implanted in other extra-pericardial locations. In this disclosure, the term "extra-pericardial locations" refers to locations in the region around, but not in contact with, the outer heart surface. The region defined as the extra-pericardial includes the gap, tissue, bone, or other anatomical features around the perimeter of, and adjacent to, but not in contact with the pericardium. These may include the superior mediastinum, middle mediastinum, posterior mediastinum, in the sub-xiphoid or inferior xiphoid area, near the apex of the heart, or other location not in intimate contact with the heart and not subcutaneous.

LPD 16 is configured to include a housing 31, electrodes 432 and 434 coupled to the housing or formed by the housing, and a fixation mechanism (e.g., tines 35 of FIG. 3) to attach LPD 16 at a desired substernal/retrosternal location. LPD 16 may have other fixation mechanisms besides tines 35.

LPD 16 may sense electrical activity of heart 12 via electrodes 432 and 434 and provide pacing pulses to heart 12 via electrodes 432 and 434. The pacing pulses provided to heart 12 may be responsive to sensed electrical signals of the heart sensed either via electrodes 432 and 434 of LPD 16 or sensed via one or more electrode combinations of defibrillation lead 16. LPD 16 may generate and deliver pacing pulses with any of a number of amplitudes and pulse widths to capture heart 12.

LPD 16 may also analyze the sensed electrical signals from one or more of the sensing vectors of LPD 16 and/or from the IMD to detect ventricular dyssnchrony. LPD 16 may not deliver CRT therapy (e.g. fusion pacing or biventricular pacing) until LPD 16 receives a communication from IMD 414 indicating detection of ventricular dyssnchrony by IMD 414.

The configuration described above in FIGS. 7A-7C is directed to providing ventricular pacing via LPD 16. However, other LPDs 16 may be positioned further superior or inferior. In some instances, more than one LPD 16 may be utilized for dual chamber pacing, e.g., with one LPD 16 providing atrial pacing and the other LPD 16 providing ventricle pacing. Alternatively, LPD 16 may be positioned over the ventricle and include a small tether extending up to the atrium with an electrode on the tether. LPD 16 could sense and/or pace via the electrode on the tether. As another alternative, LPD 16 could be elongated to serve this purpose under the sternum, so that there is one or more electrodes on the housing that senses/paces one of the heart chambers and one or more electrodes on the housing that senses/paces ventricle. In yet further embodiments, LPD 16 may be used in combination with a pacing lead implanted substernally to provide dual chamber pacing.

ICD 414 may include a housing that forms a hermetic seal that protects components of IMD 414. The housing of IMD 414 may be formed of a conductive material, such as titanium. IMD 414 may also include a connector assembly (also referred to as a connector block or header) that includes electrical feedthroughs through which electrical connections are made between conductors within the lead 416 and electronic components included within the housing. As will be described in further detail herein, housing may house one or more processors, memories, transmitters, receivers, sensors, sensing circuitry, therapy circuitry and other appropriate components. The housing 434 is configured to be implanted in a patient, such as patient 414.

Lead 416 includes a lead body that includes electrodes 424, 428 and 430 located near the distal lead end or elsewhere along the length of the lead body. The lead bodies of lead 416 also contain one or more elongated electrical conductors (not illustrated) that extend through the lead body from the connector assembly of IMD 414 provided at a proximal lead end to one or more electrodes of lead 416. The lead bodies of lead 416 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

The one or more elongated electrical conductors contained within the lead bodies of lead 416 may engage with respective ones of electrodes 424, 428, and 430. In one example, each of electrodes 424, 428, and 430 is electrically coupled to a respective conductor within its associated lead body. The respective conductors may electrically couple to circuitry, such as a therapy module or a sensing module, of IMD 414 via connections in connector assembly, including associated feedthroughs. The electrical conductors transmit therapy from a therapy module within IMD 414 to one or more of electrodes 424, 428, and 430 and transmit sensed electrical signals from one or more of electrodes 424, 428, and 430 to the sensing module within IMD 414.

The examples illustrated in FIGS. 7A-C are exemplary in nature and should not be considered limiting of the techniques described in this disclosure. In other examples, IMD 414 and defibrillation lead 416 may be implanted at other locations. For example, IMD 414 may be implanted in a subcutaneous pocket in the right chest. In this example, defibrillation lead 416 may be extend subcutaneously from the device toward the manubrium of the sternum and bend or turn and extend subcutaneously inferiorily from the manubrium of the sternum, substantially parallel with the sternum.

In the example illustrated in FIG. 7, system 400 includes an IMD system that provides, but the techniques may be applicable to other cardiac systems, including cardiac resynchronization therapy defibrillator (CRT-D) systems, cardioverter systems, or combinations thereof.

Skilled artisans appreciate that the substernal/retrosternal IMD system 400 can be configured to deliver biventricular pacing to synchronize the ventricles with each other. Biventricular pacing consists of pacing the right ventricle (RV) with a RV electrode and a left ventricle (LV) with a LV electrode. Electrodes 428 and 430 can be configured to deliver pacing pulse to the LV. The LV and/or RV is paced by separate electrodes (e.g. a LPD 16 connected through tines to the inner or outer surface of the wall of the RV, an electrode on a medical electrical lead etc.). In one or more embodiments, IMD system 400 can be configured to automatically switch between biventricular pacing and fusion pacing. Typically, the primary goal is to ensure the ventricles are synchronized with each other. Monoventricular pacing (also referred to as fusion pacing) is preferred over biventricular pacing provided the ventricles achieve synchrony. Skilled artisans appreciate that a patient's heart may require adaptive CRT in which biventricular pacing is required during one period of time (e.g. 1 hour, day, week etc.) and at another time, fusion pacing may be all that is necessary to return the ventricles to synchrony. Typically, fusion pacing involves pacing the LV; however, there are conditions in which the RV is solely paced.

Adaptive LV pacing leverages intrinsic RV conduction by pre-pacing the LV to synchronize with intrinsic RV activation. The timing of the LV pace is automatically adjusted based on the atrial to intrinsic QRS interval measurement (AV interval). One or more embodiments can set the LV pace to occur at about 70% of the intrinsic AV interval, but at least 40 ms prior to the intrinsic QRS.

One or more other embodiments can set the LV pace to occur at about a moderately lengthened QRS. For example, if the QRS width exceeds 120 ms, but does not exceed 160 ms, then LV pacing with fusion is selected. Otherwise, if the QRS width is greater than 160 ms, then biventricular (BiV) pacing is selected. Implementing a moderately lengthened QRS threshold may benefit heart failure patients. Efficacies of LV only pacing or biventricular pacing may be predicted by the moderately lengthened QRS duration. An exemplary moderately lengthened QRS corresponds to QRS width in the range of 130-150 ms. LV pacing for moderately lengthened QRS can achieve superior results compared to echocardiographic optimization.

In one or more embodiments, the intrinsic AV conduction is automatically evaluated. In one or more other embodiments, the IMD (e.g. ICD etc.), LPD and/or SD automatically evaluates intrinsic ventricular conduction based upon QRS duration from the far-field EGM or right ventricular sense to left ventricular sense (RVs-LVs) interval from the IMD sensing markers is automatically evaluated by the IMD or SD. U.S. Pat. No. 4,374,382 issued to Markowitz et al. describes IMD sensing markers, which is incorporated by reference in its entirety. Based on the results, fusion pacing (i.e. LV only pacing or RV only pacing) or biventricular pacing. RVs-LVs interval not exceeding 150 ms could correspond to LV only pacing, whereas >150 ms could switch the algorithm to biventricular pacing. In one or more other embodiments, RVs-LVs interval not exceeding 80 ms corresponds to fusion pacing while greater than 80 ms switches to biventricular pacing. Typically, RVs-LVs are shorter than the corresponding QRS width. Therefore, it takes about 40 ms to sense the onset of QRS in the RV and the final portion of the QRS in the LV is also sensed prior to the QRS end.

In one or more other embodiments, the IMD (e.g. SD 30) can track the moderately lengthened QRS over time and then relies on trend data to switch between biventricular pacing and fusion pacing. For example, assume that the moderately lengthened QRS is 120 ms, 125 ms, 130 ms, 135 m, 140 ms, and 145 ms, respectively for 6 consecutive weeks. The increasing trend could trigger the switch to biventricular pacing before the threshold is met for switching to biventricular pacing.

In another embodiment, the SD 30 could send a control signal to the LPD 16 to initiate CRT. The LPD 16 could sense a cardiac signal (i.e. a second electrical signal) from the heart of the patient. Based on the cardiac signal, the LPD 16 could determine whether to deliver CRT to the heart from the LPD 16. For example, the LPD, based on the second electrical signal, could determine that CRT is not necessary. The LPD could consider whether sensed data meets a pre-specified threshold. For instance, if the QRS width does not exceed 120 ms, the LPD 16 may withhold the delivery of CRT therapy (e.g. the LPD could then signal the SD that CRT should not be delivered based upon the cardiac signal. The SD can be configured to perform a more detailed analysis in which at least one or more parameters (such as at least two parameters) are evaluated. The SD could then send another command signal that confirms, denies or overrides the LPD 16.

In another embodiment, the LPD 16 could sense a cardiac signal that indicates a switch between fusion pacing to biventricular pacing should occur and would signal the SD. The SD could be configured to send an override signal to the LPD unless certain conditions are met.

In yet another embodiment, the LPD 16 could determine that biventricular pacing is required over fusion pacing in contravention to the SD 30 communication. In one embodiment, the LPD 16 would deliver biventricular pacing. In one or more other embodiments, the LPD 16 could determine that fusion pacing is required over biventricular pacing in contravention to the SD 30 communication. In this scenario, the LPD 16 could deliver fusion pacing.

In another embodiment, the SD transmits a control signal to the LPD to initiate CRT. The LPD senses a cardiac signal (i.e. a second electrical signal) from the heart of the patient. Based on the cardiac signal, the LPD could determine whether to deliver CRT or the type of CRT to deliver to the heart from the LPD. In one or more embodiments, the LPD, based on the second electrical signal, could initially determine that CRT is not necessary. The initial determination by the LPD could use very simplified tests such as a threshold of one or more parameters. In one or more embodiments, the SD could perform a more detailed analysis as to whether CRT should be delivered. Using the sensed data from the LPD and/or SD, the SD could generate another signal to the LPD that either confirms, denies or overrides the LPDs initial determination.

In another embodiment, the LPD could sense a cardiac signal that indicates a switch should occur between fusion pacing to biventricular pacing. Determining whether to switch between fusion pacing and biventricular pacing could be determined based upon one or more parameters (e.g. moderately lengthened QRS, etc.). The LPD could be configured to either automatically switch between fusion pacing and biventricular pacing or to wait until the SD confirms or denies switching between the CRT pacing mode (i.e. fusion pacing and biventricular pacing). The SD could be configured to send a confirmatory signal or a signal denying the LPD switching the pacing mode.

In yet another embodiment, the LPD could determine that biventricular pacing is required over fusion pacing in contravention to the SD communication. In one embodiment, the LPD would deliver biventricular pacing. In one or more other embodiments, the LPD could determine that fusion pacing is required over biventricular pacing in contravention to the SD communication. In this scenario, the LPD could deliver fusion pacing.

In one or more other embodiments, SD is implanted into or near a patient's heart. For example, the SD could be a conventional ICD or a SD described herein). Electrical signals are then sensed which includes moderately lengthened QRS duration data from the patient's heart. A determination is made as to whether cardiac resynchronization pacing therapy (CRT pacing) is appropriate based upon the moderately lengthened QRS duration in the sensed electrical signals. The CRT pacing pulses are delivered to the heart using electrodes. In one or more embodiments, the SD can switch between fusion pacing and biventricular pacing based upon data (e.g. moderately lengthened QRS, etc.) sensed from the heart.

There are many different embodiments that may be implemented with the methods described herein. One or more LPDs carrying one or more electrodes may be implanted within various chambers of the heart of the patient or otherwise in close proximity of the cardiac muscle. At these locations, an LPD may sense ECG signals with high signal-to-noise ratios to detect arrhythmias. In addition, an LPD may provide cardiac pacing at the location of the implanted LPD. In some examples, one or both of SD and LPD may share detected signals or physiological information (e.g., R-R intervals, electrogram morphology measurements, and/or electrocardiograms or electrograms) such that the device receiving such information can determine a condition of patient 14 (e.g., determine whether or not patient 14 is experiencing an arrhythmia and or lack of synchrony between ventricles). Communication between an LPD and a SD is described in U.S. Pat. No. 8,744,572, filed on Jan. 31, 2013, incorporated herein in its entirety.

In some examples, communication between the SD and an LPD may be used to initiate therapy and/or confirm that therapy should be delivered. The SD may also transmit a communication message to the LPD instructing the LPD to change one or more parameters that define the CRT therapy. In this one-way communication example, the SD may be configured to transmit communications to the LPD and the LPD may be configured to receive the communication from the SD. Alternatively, one-way communication may be established such that the LPD may be configured to transmit communications to the SD (e.g., communication from LPD 16). In other examples, two-way communication may allow confirmation of a detected of a cardiac condition (e.g. ventricular dyssynchrony, tachyarrhythmia, bradycardia etc.) prior to delivery of any therapy. Communication between the SD and the LPD is described in greater details in U.S. Pat. No. 8,744,572 filed May 26, 2013 and entitled "SYSTEMS AND METHODS FOR LEADLESS PACING AND SHOCK THERAPY", incorporated by reference in its entirety.

The systems and techniques described herein may be generally related to cooperative monitoring of a patient and/or therapy delivery to the patient using multiple implanted devices such as an SD and an LPD. In one example, the SD and LPD may detect the functions of each other and/or communicate to coordinate monitoring and therapy such as CRT. However, the SD and LPD may coordinate other monitoring and therapy features. For example, using the communication techniques described herein, prior to either the SD or LPD delivering therapy, sensed data from both devices may be used to determine if the therapy should be delivered. In some examples, the SD or the LPD may be configured to override the other device in situations in which there is a discrepancy between whether or not physiological condition is occurring. In any case, the SD and LPD may be configured to function together to monitor and/or provide therapy to patient 14.

The techniques described herein may provide for a SD 30 and LPD 16 to operate cooperatively within a patient to monitor the heart for arrhythmias and deliver appropriate therapy to treat any detected arrhythmias. For example, an SD 30 and LPD 16 may detect ventricular dyssynchrony and deliver CRT. Wireless communication between the SD implanted external of the rib cage and one or more LPDs implanted within the heart may provide various ECG or EGM sensing vectors.

Using a RV lead to deliver pacing pulses to the RV may be unnecessary for CRT patients who exhibit left bundle branch block (LBBB) and/or an average PR interval less than (<) 230 ms. Accordingly, the present disclosure is configured to eliminate the RV lead in pacing system 10 to deliver pacing pulses (e.g. CRT pacing such as LV only pacing or biventricular pacing etc.). As previously described, system 10 is configured to include one or more ventricular pacing electrode(s) (e.g. LV pacing lead, leadless pacing electrode such as MICRA™) disposed in or on ventricular tissue (e.g. LV) and one or more sensing electrodes strategically positioned to sense heart activity. Since pacing systems 10 lack a RV lead, method 300, shown in FIG. 8, estimates RV-timing through data acquired from CRT patients in which a RV lead is employed. The CRT data that is acquired from numerous patients is stored into memory of the IMD (preferably, IMD is the SD 30 but can be LPD 16) and/or the memory associated with a computing device such as a programmer. The data is accessed by a processor of a computing device (IMD (e.g. SD 30) or external to the patients' body such as a programmer etc.) to determine how to estimate RV timings for a particular patient.

Method 300 begins during or after the implantable medical device(s) (e.g. pacemaker such as SD 30, etc.) has been implanted into the patient. For example, method 300 can also be implemented to adjust the timing of CRT pulses when a patient has a follow-up visit to reprogram the IMD. While method 300 is generally described as the SD 30 processor executing the computer instructions of method 300 for determining the timing of the CRT pacing pulses, skilled artisans understand that other therapy delivery device processors can also be used to determine the timing of the CRT pacing pulses for method 300. Additionally, method 300 is not limited to the FIGS. 1-7 embodiments in which LPD 16 is affixed to a wall (e.g. an inner wall or outer wall) of the left ventricle and in wireless communication with SD 30. Other configurations can be used such as, for example, the RV can undergo fusion pacing instead of LV fusion pacing. Additionally, one or more LPD 16 can be placed on an outer wall of the LV and/or RV.

Method 300 begins at block 302 in which heart activity is sensed from the patient's heart by strategically placed pairs of electrodes coupled to the processor through channels. Each channel, configured to receive an electrogram signal, includes positive and negative sensitivity thresholds (dashed horizontal lines shown in FIG. 9) that activate the timer thread when a sensed signal exceeds one of the sensitivity thresholds.

Referring to FIG. 9, exemplary set of electrograms 200, generated from each pair of electrodes over a single channel. For example, P-wave data 202 (i.e. atrial sense data acquired from, for example, the right atrium using electrodes in proximity to, or on the RA tissue) is acquired from an atrial near-field electrogram 202 shown in FIG. 9. Atrial near-field electrogram 202 is generated through a signal conducted to the IMD processor via a pair of electrodes (e.g. tip to ring electrodes located on the atrial lead) in proximity or in direct contact to atrial tissue. Exemplary atrial event data (e.g. As) is obtained from the atrial near field electrogram via electrodes (e.g. non-contact sub-sternal electrodes) by the IMD processor working in conjunction with a timer thread. A timer thread is a unique process, task or routine that may operate independent of other processes or threads. For example, a timer thread is configured to measure time intervals.

The timer thread seeks As data that exceeds positive and/or negative thresholds that are shown in dashed lines 212a, b respectively. Once the As data exceeds the threshold 212a, b, the timer thread starts timing from the As event to measure an interval. A detailed explanation of interval measurements can be found in a manual for CRT-D devices entitled AMPLIA MRI™ QUAD CRT-D SURESCAN™ DTMB2Q1 (hereinafter "Medtronic AMPLIA™ manual") (2016) available from Medtronic, Inc. located in Minneapolis, Minn. and is incorporated by reference in its entirety. AMPLIA™ MRI™ CRT-D devices can be configured to implement DDD pacing mode or VDD pacing mode, as described in the Medtronic AMPLIA™ manual. Additionally, AMPLIA™ MRI™ CRT-D devices can be configured to implement RV pacing or LV pacing.

The timer thread stops once Qon exceeds its sensitivity thresholds 214a,b associated with its channel to measure the AV interval. The processor for the IMD then causes the measured As-Qon interval (i.e. 160 ms) to be stored into memory of the IMD. Signal processing methods that can be used to estimate QRS onset (Qon) from electrode channels measuring ECG or EGM signals are described in U.S. Pat. No. 9,132,274 incorporated by reference herein in its entirety. Another timer thread stops once LV-s exceeds one of its sensitivity thresholds associated with LV sense (LV-s). The processor for the IMD (e.g. SD 30) causes the measured As-LVs interval (i.e. 280 ms as denoted as reference numeral 5 on FIG. 9) from As to LVs to be stored into memory of the IMD (e.g. memory of the SD 30). Left ventricular sensed data (LV-s) accessed from LV near field electrogram 206 depicted in FIG. 9, was generated from a bipolar signal transmitted from tip to ring electrodes located on the LV lead bipolar lead.

Referring to the far field electrogram 204, the onset of QRS data (Qon) is shown at reference numeral 2 while the Q wave is detected at reference numeral 3 on FIG. 9.

Alternatively, Qon can be measured from the substernal electrodes. An example of detection QRS onset data may be seen with respect to U.S. Pat. No. 9,132,274 issued Sep. 15, 2015, entitled DETERMINING ONSETS AND OFFSETS OF CARDIAC DEPOLARIZATION AND REPOLARIZATION WAVES and assigned to the assignee of the present invention, the disclosure of which is incorporated by reference in its entirety herein. At block 304, the atrial event to onset of QRS interval, shown as As-Qon at reference numeral 6 on FIG. 9, is measured by the IMD processor (e.g. SD 30) accessing the data from IMD memory. For example, the IMD processor acquires the time of the atrial event (atrial sense (As) or atrial pace (Ap)) and the time of QRS onset. The IMD processor is then configured to measure the interval between the time of As and the time of the onset of QRS. Referring to FIG. 9, the As-Qon interval is 160 ms.

At block 306, the P-wave to LVs wave interval (e.g. As-LVs) is measured as described herein to any of the pacing configurations. The preferred embodiment(s) is any of the subcutaneous pacing system embodiments, described herein, in which non-contact substernal electrodes are employed to sense atrial activity. Another embodiment for implementing the instructions associated with any method herein can comprise a DDD pacemaker that employs a RA lead and a LV lead and no RV lead. The far field electrogram that comprises the Qon data can be acquired from the Can LV tip electrodes of the LV lead. The LV sensing data can be acquired from LV lead electrodes such as LV tip-LV ring electrodes. In one or more other embodiments, a SD 30 in electrical communication with a LPD disposed in or on the LV can be employed. In the SD 30 and LPD 16 embodiment, atrial sensed data is acquired from P-waves associated with a far-field vector of SD 30 (e.g. Can-D1). The far-field electrogram (for obtaining Q on) can be the same electrogram vector Can-D1. Alternatively, the far-field electrogram (for obtaining Q on) can be one of the substernal vectors S1-S2, and LV sensing is acquired from the LPD.

The processor of the IMD accesses the interval data stored in memory. Referring to reference numeral 6 on FIG. 9, the exemplary As-LVs is 280 ms.

At block 308, the AV interval (e.g. A-RV) is estimated by the IMD processor. Estimating A-RV comprises a series of calculations by the processor of the IMD accessing data from the memory of the IMD. For example, (As-Qon+t) is subtracted from (As-LVs) to obtain an estimated AV interval 208, as shown by dashed lines at electrogram 202. In FIG. 9, "t" equals 30 ms.

(As-Qon+t) is calculated in which t is set to 30 ms (or about 30 ms) as shown in FIG. 9. As-Qon was previously measured (i.e. 160 ms) at block 304 and stored into the memory of the IMD. Time constant "t", stored into the memory of the IMD, is derived from a population of patients that use a RV lead. Time constant t represents a difference between onset of QRS and RV sense timing as determined through data collected from a group of patients having an implanted RV lead. Time constant "t" is applied as a correction factor to obtain a new As (Ap)-LVs timing or AV interval.

Referring to reference numeral 8 of FIG. 9, the difference is calculated as follows:

$$d = \text{As-LVs} - (\text{As-Qon} + 30 \text{ ms}) = 280 \text{ ms} - 190 \text{ ms } d = 90 \text{ ms}.$$

Skilled artisans appreciate that the 90 ms is only one example and many different examples can provide different results based upon a particular patient.

At block 310, the new delay (e.g. SAV and/or PAV), estimated at block 308, is saved into the memory of the IMD (e.g. SD 30). The IMD (e.g. SD 30) processor applies the correction factor, "d", to LV sensing AV delays (As-LVs) to estimate the RV sensing AV delays (As-RVs). In the absence of the RV lead, the periodic measurements required by the computer instructions and executed by the IMD (e.g. SD 30) processor, are as follows:
As-LVs and As-Qon $$d = \text{As-LVs} - (\text{As-Qon} + t) \text{ where "}t\text{" can be equal to 30 ms}$$

$$\text{As-RVs(estimated)} = \text{As-LVs} - d$$

The IMD processor (e.g. SD 30 etc.) may determine the new AV delay based on As-LVs−d. For example, the IMD processor can set the new AV delay to a certain percentage (e.g. 70%) of (As-LVs−d) that would be (0.70)*(280 ms−90 ms)=133 ms. As-Qon may be measured less frequently (e.g. once a day, because it's a derived measure from EGMs) while As-LVs (direct result of sensing delays) may be measured every minute. The most recent value of the correction factor d will be stored in memory and applied to get the value of the new AV delay every minute. Relative to atrial pacing, As will be replaced by Ap.

The newly determined pacing delay may be configured for CRT therapy such as LV only pacing or biventricular pacing.

At block 312, CRT pacing pulses are then delivered to the heart using the new pacing parameter (e.g. As (Ap)-LVs timing). Thereafter sensing subsequent electrical signals from the patient's heart using the IMD (e.g. SD, leadless pacing device etc.). The SD, based on the subsequent electrical signals, determines whether the CRT pacing by the LPD 16 provided efficacious resynchronization and whether the delivery and timing of subsequent CRT pacing pulses should be modified.

At decision block 318, the IMD processor (SD 30) determines whether a time delay 1 has expired. The purpose of decision block 318 is to determine the period after which the IMD (SD 30) will make the checks for measuring time interval from atrial event to left ventricular sensing time and accordingly update the AV delay for pacing using that measurement and the latest measurement of As-Qon that is available. Delay 1 can be preset to any value. One exemplary value may be 1 minute. Delay 1 can also be 2 minutes, 3 minutes . . . 1 hour etc.) If sufficient time (e.g. 1 minute) has expired, the YES path continues to block 306. If not, the NO path continues to block 312.

At decision block 319, a IMD (e.g. SD 30) processor determines whether a time delay 2 has expired. The purpose of decision block 319 is to determine the period after which the IMD (e.g. SD 30) processor will check for measuring timing interval from atrial event to onset of QRS on the far-field vector and accordingly update the measurement As-Qon. Delay 2 can be preset to any time value (e.g. 1 week, 2 weeks etc.). One exemplary time value can be 1 week. If sufficient time (e.g. 1 week) has expired at block 319, the computer instructions executed by the IMD processor (e.g. SD) follows the YES path to block 304. If not, the computer instructions executed by the IMD processor (e.g. SD) follows the NO path to block 312.

FIG. 10 is a flow diagram that depicts method 500 for efficiently updating one or more pacing parameters (e.g. AV delays) using a LV only pacer or pacing system 10 without using a RV lead. Method 500 does not perform a Qonset as frequently as method 300. Instead, the device (e.g. SD 30) or pacing system 10 performs a one-time difference "d" calculation between LVs time and the estimated RV time and applies that difference to each subsequently measured As-LVs. Accordingly, the device avoids the need to determine Q-on more frequently (e.g. once every minute) and can do at a lesser frequency (e.g. once every day or once every week). Instead, the device can perform the method once every week (i.e. at a lesser frequency) than more frequently performing method 300. From the implementation standpoint, avoiding performing a Qon evaluation more frequently (e.g. once every minute) saves power and reduces the complexity of implementation.

The method 500 is the same or similar to method 300 except as to the frequency of the calculations. The description of method 300 is incorporated herein by reference except as shown as to the frequency of calculations. Method 500 begins with block 502 in which a difference "d" is determined between LV sensing and estimated RV sensing times as shown in FIG. 9. The computer instructions then cause IMD processor to calculate delays at block 504. Optimal pacing delays SAV/PAV are calculated based on As-LVs-d (e.g. 0.7*(As-LVs-d). More specifically, 70% is applied to the result, which is obtained from subtracting the atrial event to Qon interval and a time interval "t" from the atrial event to LVs interval. For example, if the result (i.e. step 4 of claim 34) is 200 ms, then the new AV delay for left ventricular pacing will be 140 ms (i.e. 0.70*200 ms=140 ms).

The new pacing delay(s) is stored into memory of the implantable medical device (e.g. SD 30 or LPD 16). Using the processor of the IMD, CRT pacing then employs the new pacing delay at block 506. A determination is then made as to whether a delay (e.g. about one (1) minute delay etc.) has passed at block 508. If so, the LV only pacing is paused or suspended at block 510 so that As-LVs can be measured for 1 beat (or a few beats) using the techniques described herein. If the time delay (e.g. 1 minute etc.) has not expired, the return path continues to block 506 to deliver pacing therapy. Returning to the block in which "d" is calculated, if a predetermined amount of time (e.g. 1 week or other time period set by the physician or preset by the device manufacturer) has elapsed at block 512, the d calculation is repeated.

Simplified CRT systems can be configured to effectively implement CRT without using a RV lead. Adaptive CRT has shown that RV pacing component of resynchronization therapy is unnecessary in a substantially large patient group, which leads to the idea of having a simplified lower-cost resynchronization system without a RV pacing electrode. CRT timings require estimation of RV sensing. As previously stated, exemplary simplified systems 10 are configured to perform LV-DDD, VDD pacing or leadless ventricular pacing (e.g. LV pacing) in systems without a RV lead.

Electrical activation time or local electrical activity is determined relative to timing of a fiducial, an indicator of a global cardiac event (e.g. timing of activation of a chamber of the heart, timing of pacing of a chamber of the heart, etc.). For example, the fiducial may be the onset of QRS, the peak of QRS (e.g. minimum values, minimum slopes, maximum slopes), zero crossings, threshold crossings, etc. of a near or far-field electrogram (EGM), onset of application of a pacing electrical stimulus, or the like.

After electrocardiogram (ECG) data has been extracted from the first electrical signal for an intrinsic rhythm during a conduction test beat (or without a conduction test beat), the ECG data is filtered with a low pass filter. For instance, the low pass filter could be implemented as a moving average executed in two loops of method 500. The number of samples in the moving average could be adjusted to achieve good attenuation at 50 Hz and 60 Hz line frequencies for the sampling rate set, for example, at 256 Hz. The time derivative of the signal (dV/dt) can then be calculated using conventional methods. Fiducial points associated with a QRS complex or P-wave can be determined by finding the samples for which the derivative is outside the predetermined boundaries, as described in U.S. Pat. No. 7,941,218 to Sambelashvili, incorporated by reference in its entirety.

The processor 70 of the SD 30 retrieves the data from the first electrical signal (i.e. baseline) from memory 72 and a determination is made by the SD 30 as to the appropriate timing in which electrical stimuli (e.g. pacing pules etc.) are delivered to cardiac tissue by the LPD 16. The timing of the delivery of pacing pulses can be predetermined and stored as a lookup table into the memory 72 of the SD 30 and/or the LPD 16. The timing could be also programmable by the user of the system. For example, the timing of pacing by the LPD 16 can be optimized by delivering pacing at a pre-specified interval after the end of a P-wave. The pre-specified interval is either a fixed number or calculated by the SD 30 from widths of the P-wave and paced QRS complex. In one or more embodiments, pre-specified interval fixed number ranges from about 0 ms to about 60 ms and can be typically set at about 30 ms. Alternatively, the timing of pacing by LPD 16 can be optimized by delivering pacing at a pre-specified interval relative to the onset of the QRS complex. The pre-specified fixed number can range from 0 to 60 ms and is typically set at 0 ms.

In sum, the LPD 16, in communication with SD 30, is configured to pace relative to fiducial points with pre-specified intervals (e.g. at the detected onset of QRS, 30 ms after the detected end of the P-wave or another suitable rule for timing of pacing).

The SD 30 then wirelessly sends a command signal to the LPD 16 to deliver electrical stimuli (e.g. pacing pulses) to the tissue surrounding LPD 16. In another embodiment, LPD 16 can operate without SD 30. In this embodiment, LPD 16 determines when and how to deliver the pulses to the target tissue.

Additionally, method 300 and/or method 500 can be configured to determine whether CRT therapy is effectively treating the patient. Fusion pacing is deemed to successfully treat ventricular dyssynchrony when the QRS complexes sensed during pacing are sufficiently different from QRS complexes of the intrinsic rhythm. Wavelet analysis can be used to perform the QRS complex comparison, as described in U.S. Pat. No. 6,393,316 to Jeffrey Gillberg et al., incorporated by reference. Wavelet analysis can quantify fusion and optimize timing as described in U.S. Pat. No. 8,145,308, incorporated by reference in its entirety. Additionally, AV intervals can be optimized through U.S. Pat. No. 8,214,041 to Van Gelder et al. incorporated by reference in its entirety.

While method 300 is described relative to system 10 that comprises a subcutaneous device (SD) in a patient, and a leadless pacing device (LPD) in the patient's heart, skilled artisans understand that the present disclosure can be implemented with any pacing configuration that lacks a RV lead. For example, method 300 and/or 500 can be executed solely by a processor contained within implantable medical device (e.g. pacemaker, ICD etc.). One exemplary IMD that can implement method 300 and/or 500 can be solely performed by LPD 16. The LPD can be positioned in or on cardiac tissue (e.g. LV, RV, LA, RA) to perform cardiac therapy (e.g. CRT, His bundle pacing, pacing, to address bradycardia, anti-tachycardia pacing. One exemplary location to position the LPD can be the Triangle of Koch tissue to perform cardiac therapy (e.g. ventricle-from-atrium (VfA) cardiac therapy) as shown and described in U.S. Patent Application Ser. Nos. 62/647,426, 62/647,441, 62/647,414, Ser. No. 15/934,517, filed on Mar. 23, 2018, and incorporated by reference in their entirety. A processor is employed in the implantable medical device (IMD) such as SD (or LPD alone) to determine whether cardiac resynchronization pacing therapy (CRT pacing) is appropriate based upon the sensed heart activity.

The SD can be employed to determine timing of CRT pacing pulses for delivery to cardiac tissue through the LPD and sending signals indicative thereof to the LPD. The timing of the CRT pacing pulses comprises a set of instructions executed by the SD microprocessor.

Skilled artisans appreciate that the disclosure can be implemented using many different types of substernal leads. For example, FIG. 7D depicts an undulating substernal lead used in cardiac system 400.

One or more other embodiments are directed to a cardiac system 400 that includes an undulating medical electrical lead extending from implantable cardioverter-defibrillator (ICD) 9. An extravascular implantable electrical lead having an undulating configuration is described in US 2016-0158567 A1, entitled "EXTRAVASCULAR IMPLANTABLE ELECTRICAL LEAD HAVING UNDULATING CONFIGURATION" filed Dec. 9, 2015, incorporated by reference in its entirety.

Lead 480 includes a defibrillation electrode formed from two defibrillation electrode segments 28a and 28b (also referred to as defibrillation segments D2, and D1 respectively). The defibrillation electrode segments 28 extend along a substantial part of undulating portion 442, e.g., along at least 80% of undulating portion 442. The defibrillation electrode segment 28a extends along a substantial portion of undulation from the proximal end of undulating portion, except for the part of undulating portion that includes the gap 450 where electrode 31b is disposed. In one embodiment, gap 450 and electrode 31b can be located along the part of undulating portion 42 that transitions from peak to peak. Lead 480 also includes two pace/sense electrodes 31a and 31b. The electrodes 31a and 31b can be disposed along the undulating configuration 42 such that each electrode 31a and 31b is substantially aligned or otherwise disposed along the major longitudinal axis "x." The orientation of electrodes 31a and 31b can be configured differently even though they are substantially disposed at substantially the same horizontal position when the distal portion is implanted within the patient. Moreover, electrodes 31 are disposed along the undulating configuration 42 at locations such that the electrodes 31 will be substantially aligned with one another along the anterior median line instead of the left sternal line. In this case, the defibrillation electrode segment 28a is disposed along the peak 24a and will extend toward the left side of the sternum when implanted and defibrillation electrode segment 28b is disposed along the peak 24b and will extend toward the right side of the sternum when implanted.

Defibrillation electrode segments 28 and pace/sense electrodes 31 may include the structure and functionality described above with respect to FIGS. 7A-D, including but not limited to the spacing between segments 28 and electrodes 31, the size of segments 28 and 31, electrode and lead body dimensions, spacings, materials, shapes, and the like. Additionally, as described above with respect to FIGS. 7A-D, in some configurations defibrillation electrode segments 28 may each be connected to a common conductor such that a voltage may be applied simultaneously to all the defibrillation electrode segments 28 (and they function as a single polarity) to deliver a defibrillation shock to a patient's heart. In other configurations, the defibrillation electrode segments 28 may be attached to separate conductors such that each defibrillation electrode segment 28 may apply a voltage independent of the other defibrillation electrode segments 28. In this case, ICD 9 or lead 480 may include one or more switches or other mechanisms to electrically connect the defibrillation electrode segments together to function as a common polarity electrode such that a voltage may be applied simultaneously to all the defibrillation electrode segments 28 in addition to being able to independently apply a voltage.

Each electrode 31 is substantially aligned along a major longitudinal axis ("x"). In one example, the major longitudinal axis is defined by a portion of the elongate lead body, e.g., the substantially linear portion 21. In another example, the major longitudinal axis is defined relative to the body of the patient, e.g., along the anterior median line (or midsternal line), one of the sternal lines (or lateral sternal lines), left parasternal line, or other line. The electrodes 31a and 31b may be disposed along the undulating configuration 22 such that each electrode 31a and 31b is substantially aligned or otherwise disposed along the major longitudinal axis "x." In one configuration, the midpoint of each electrode 31a and 31b is along the major longitudinal axis "x," such that each electrode 31a and 31b is at least disposed at substantially the same horizontal position when the distal portion is implanted within the patient. In other configurations, the electrodes 31 may be disposed at any longitudinal or horizontal position along the distal portion disposed between, proximal to, or distal to the defibrillation electrode segments 28, as described in other embodiments herein. In the example illustrated in FIGS. 7A-D, the electrodes 31 are disposed along the undulating configuration 22 at locations that will be closer to the heart of the patient than defibrillation electrode segments 28. As illustrated in FIG. 7D, for example, the electrodes 31 are substantially aligned with one another along the left sternal line. The defibrillation electrode segments 28 are disposed along the peaks that extend toward a right side of the sternum away from the heart. This configuration places the pace/sense electrodes 31 at locations closer to the heart and thereby lower pacing thresholds and better sense cardiac activity of the heart.

Skilled artisans appreciate that while methods 300 and 500 have been described as the SD processor implementing the processing steps, skilled artisans can appreciate that LPD 16 can be configured to also implement the processing steps.

The techniques described in this disclosure, including those attributed to the IMD 16, the programmer 24, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure. System 10 provides a low-cost, less complex, and more simplified resynchronization solution for developing and a portion of the developed markets.

While method 300 is described relative to LPD 16 placed in the left ventricle, skilled artisans appreciate that the present disclosure can be applied to many different embodiments in which SD 30 is used in combination with LPD 16. For example, the LPD can be implanted within a chamber of the heart or substernally/retrosternally, as described in U.S. provisional patent application Ser. No. 61/819,946 filed May 6, 2013 and entitled "IMPLANTABLE MEDICAL DEVICE SYSTEM HAVING IMPLANTABLE CARDIAC DEFIBRILLATOR SYSTEM AND SUBSTERNAL LEADLESS PACING DEVICE", incorporated by reference in its entirety, U.S. provisional patent application Ser. No. 61/820,024 filed May 6, 2013 and entitled "ANCHORING AN IMPLANTABLE MEDICAL DEVICE WITHIN A SUBSTERNAL SPACE, and U.S. provisional patent application Ser. No. 61/820,014 filed May 6, 2013 and entitled "SYSTEMS AND METHODS FOR IMPLANTING A MEDICAL ELECTRICAL LEAD WITHIN A SUBSTERNAL SPACE", all of which are incorporated by reference herein. The SD is configured to deliver shocks to the patient without any leads implanted within the vasculature and/or heart of the patient.

Skilled artisans appreciate that while the new AV delay may be 0.7 (As-LVs-d), the percentage of can be different than 70%. For example, it may be determined that a different percentage can be used (e.g. up to 65%, up to 75%, up to 80%, up to 85%).

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A method of using a subcutaneous device (SD) in a patient and a leadless pacing device (LPD) coupled to a patient's heart comprising:
   sensing heart activity including atrial and ventricular events from the patient's heart using the SD;
   sensing left ventricular events (LVs) using the LPD;
   determining whether cardiac resynchronization pacing therapy (CRT pacing) is appropriate based upon the heart activity sensed using the SD;
   determining timing of CRT pacing pulses for delivery to cardiac tissue through the LPD, wherein determining the timing of the CRT pacing pulses comprises:
   (1) detecting an atrial event and determining onset of baseline QRS (Qon) from the heart activity sensed using the SD;
   (2) measuring an atrial event to Qon interval;
   (3) measuring an atrial event to LVs interval;
   (4) subtracting the atrial event to Qon interval and a time interval "t" from the atrial event to LVs interval to obtain a correction factor; and
   (5) using the correction factor to obtain a new pacing delay;
   thereafter delivering CRT pacing pulses to the heart using the LPD and using the new pacing delay;
   thereafter sensing subsequent heart activity from the patient's heart using the SD; and
   determining, by the SD based on the subsequent sensed heart activity, whether the CRT pacing pulses delivered using the LPD using the new pacing delay provided efficacious resynchronization and whether the delivery and timing of subsequent CRT pacing pulses should be modified.

2. The method of claim 1 wherein the new pacing delay comprises one of an atrioventricular delay (AV delay) and an interventricular delay (VV delay).

3. The method of claim 1 wherein a right ventricular lead (RV lead) is not used to sense RV activity.

4. The method of claim 1 further comprising:
   ensuring continuous synchronized CRT delivery by the LPD periodically evaluating intrinsic conduction data monitored through the SD.

5. A method of claim 1 further comprising:
   sensing electrical signals from a substernally placed lead extending from the SD.

6. The method of claim 1 wherein the LPD is in contact with a wall of a left ventricle.

7. The method of claim 1 wherein DDD pacing mode is employed.

8. The method of claim 1 wherein VDD pacing mode is employed.

9. The method of claim 1 further comprising:
   responsive to determining by the SD that the CRT pacing by the LPD does not provide efficacious resynchronization, switching the CRT pacing delivered by the LPD from a first mode to a second mode.

10. The method of claim 8 wherein the switching of CRT pacing mode comprises switching between fusion pacing and biventricular pacing.

11. The method of claim 1, wherein the at least one electrode is configured to deliver pacing therapy to the left ventricle of the patient's heart.

12. The method of claim 1, wherein a therapy delivery module is configured to deliver bi-ventricular pacing therapy to the patient's heart, and wherein a control module is configured to initiate the delivery of bi-ventricular pacing therapy to the patient's heart.

13. A method of using an implantable medical device (IMD) in the patient's heart comprising:
   sensing heart activity from the patient's heart using a plurality of electrodes;
   employing a processor in the IMD to determine whether cardiac resynchronization pacing therapy (CRT pacing) is appropriate based upon the sensed heart activity;
   employing the IMD to determine timing of CRT pacing pulses for delivery to cardiac tissue through one or more pacing electrodes from the plurality of electrodes; the IMD processor configured to adjust timing of the CRT pacing pulses comprising:
   (1) determining onset of baseline QRS timing from the sensed heart activity;
   (2) measuring As-onset of baseline QRS (Qon) timing;
   (3) measuring baseline As (Ap)-LVs timing;
   (4) subtracting As(Ap)+Qon+t timing from the As(Ap)-LVs timing to obtain a result where t is a constant parameter representing a difference between onset of QRS and RV sense timing from data collected from a group of patients having an implanted RV lead;
   (5) delivering the CRT pacing pulses to the heart using the IMD and based on subtracting the result in from step 4 from a subsequent As (Ap)-LVs timing measurement;
   thereafter sensing subsequent electrical signals from the patient's heart using the IMD; and
   determining, by the IMD based on the subsequent electrical signals, whether the CRT pacing by the IMD provided efficacious resynchronization.

14. Cardiac pacing system comprising:
a leadless pacing device (LPD); and
a subcutaneous device (SD) comprising:
- a sensing module comprising a sensing circuit for acquiring heart activity including atrial and ventricular events from the patient's heart using the SD and using the LPD to acquire left ventricular events (LVs); and
- a control module comprising a therapy circuit configured to:
  - (a) determine whether cardiac resynchronization pacing therapy (CRT pacing) is appropriate based upon the heart activity sensed using the SD;
  - (b) determine timing of CRT pacing pulses for delivery to cardiac tissue through the LPD, wherein determining the timing of the CRT pacing pulses comprises:
    - (1) detecting an atrial event and determining onset of baseline QRS (Qon) from the heart activity sensed using the SD;
    - (2) measuring an atrial event to Qon interval;
    - (3) measuring an atrial event to LVs interval;
    - (4) subtracting the atrial event to Qon interval and a time interval "t" from the atrial event to LVs interval to obtain a correction factor; and
    - (5) using the correction factor to obtain a new pacing delay;
  - the sensing module further configured to sense heart activity from the patient's heart subsequent to delivery of CRT pacing pulses to the heart using the LPD and using the new pacing delay;

using the SD; and
the control module further configured to determine, by the SD based on the subsequent sensed heart activity, whether the CRT pacing pulses delivered using the LPD using the new pacing delay provided efficacious resynchronization and whether the delivery and timing of subsequent CRT pacing pulses should be modified.

15. The system of claim 14 wherein the new pacing delay comprises one of an atrioventricular delay (AV delay) and an interventricular delay (VV delay).

16. The system of claim 14 wherein a right ventricular lead (RV lead) is not used to sense RV activity.

17. The system of claim 14, wherein the control module is configured to
ensure continuous synchronized CRT delivery by the LPD periodically evaluating intrinsic conduction data monitored through the SD.

18. The system of claim 14, wherein the sensing module is configured to sense electrical signals from a substernally placed lead extending from the SD.

19. The system of claim 14 wherein the LPD is configured to be in contact with a wall of a left ventricle, in use.

20. The system of claim 14 wherein DDD pacing mode is employed.

21. The system of claim 20 wherein the switching of CRT pacing mode comprises switching between fusion pacing and biventricular pacing.

22. The system of claim 14 wherein VDD pacing mode is employed.

23. The system of claim 14, wherein the control module is further configured to switch the CRT pacing delivered by the LPD from a first mode to a second mode, responsive to determining by the EICD that the CRT pacing by the LPD does not provide efficacious resynchronization.

24. The system of claim 14, wherein the at least one electrode is configured to deliver pacing therapy to the left ventricle of the patient's heart.

25. The system of claim 14, wherein a therapy delivery module is configured to deliver bi-ventricular pacing therapy to the patient's heart, and wherein a control module is configured to initiate the delivery of bi-ventricular pacing therapy to the patient's heart.

* * * * *